US009855103B2

(12) United States Patent
Tsekos et al.

(10) Patent No.: US 9,855,103 B2
(45) Date of Patent: Jan. 2, 2018

(54) ROBOTIC DEVICE AND SYSTEM SOFTWARE, HARDWARE AND METHODS OF USE FOR IMAGE-GUIDED AND ROBOT-ASSISTED SURGERY

(71) Applicant: University of Houston System, Houston, TX (US)

(72) Inventors: Nikolaos v. Tsekos, Houston, TX (US); Nikhil V. Navkar, Corona, CA (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 770 days.

(21) Appl. No.: 14/011,574

(22) Filed: Aug. 27, 2013

(65) Prior Publication Data
US 2014/0058407 A1 Feb. 27, 2014

Related U.S. Application Data

(60) Provisional application No. 61/693,534, filed on Aug. 27, 2012.

(51) Int. Cl.
*A61B 5/05* (2006.01)
*A61B 19/00* (2006.01)
(Continued)

(52) U.S. Cl.
CPC .............. *A61B 19/50* (2013.01); *A61B 34/10* (2016.02); *A61B 34/30* (2016.02); *A61B 34/76* (2016.02);
(Continued)

(58) Field of Classification Search
CPC . A61B 19/22; A61B 19/2203; A61B 19/5212; A61B 19/5223; A61B 19/5244; A61B 19/54; A61B 19/56; A61B 2017/00911; A61B 2019/2223; A61B 2019/223; A61B 2019/2234;
(Continued)

(56) References Cited

U.S. PATENT DOCUMENTS

| 2003/0233039 A1 | 12/2003 | Shao et al. | |
| 2004/0009459 A1* | 1/2004 | Anderson | ........... G06F 19/3406 434/262 |

(Continued)

FOREIGN PATENT DOCUMENTS

WO 2007005367 A2 1/2007

*Primary Examiner* — Elmer Chao
(74) *Attorney, Agent, or Firm* — Eric P. Mirabel

(57) ABSTRACT

Provided herein are systems, modules and methods of using the same for in-situ real time imaging guidance of a robot during a surgical procedure. The systems comprise a plurality of modules that intraoperatively link an imaging modality, particularly a magnetic resonance imaging modality, a medical robot and an operator thereof via a plurality of interfaces. The modules are configured to operate in at least one computer having a memory, a processor and a network connection to enable instructions to generally control the imaging modality, track the robot, track a tissue of interest in an area of procedure, process data acquire from imaging modality and the robot and visualize the area and robot. Also provided are non-transitory computer-readable data storage medium storing computer-executable instructions comprising the modules and a computer program produce tangibly embodied in the storage medium.

32 Claims, 36 Drawing Sheets

(51) Int. Cl.
  *A61B 34/30* (2016.01)
  *A61B 34/00* (2016.01)
  *A61B 34/10* (2016.01)
  *A61B 17/00* (2006.01)
  *A61B 90/00* (2016.01)
  *A61B 90/30* (2016.01)
  *A61B 34/20* (2016.01)

(52) U.S. Cl.
  CPC ............... *A61B 2017/00243* (2013.01); *A61B 2034/2051* (2016.02); *A61B 2090/306* (2016.02); *A61B 2090/3614* (2016.02); *A61B 2090/374* (2016.02); *A61B 2090/378* (2016.02); *A61B 2090/3958* (2016.02)

(58) Field of Classification Search
  CPC .... A61B 2019/2242; A61B 2019/2269; A61B 2019/2288; A61B 2019/2292; A61B 2019/2296; A61B 2019/464; A61B 2019/502; A61B 2019/5236; A61B 2019/5259; A61B 2019/5287; A61B 2034/102; A61B 2090/363; A61B 34/75
  See application file for complete search history.

(56) References Cited

U.S. PATENT DOCUMENTS

| | | | |
|---|---|---|---|
| 2005/0177054 A1* | 8/2005 | Yi | A61B 5/055 600/510 |
| 2008/0161677 A1* | 7/2008 | Sutherland | A61B 19/22 600/417 |
| 2008/0287783 A1* | 11/2008 | Anderson | A61B 5/06 600/429 |
| 2011/0107270 A1 | 5/2011 | Wang | |

\* cited by examiner

| Method | time (ms) |
|---|---|
| MR projections | 20-24 |
| MR 3D DPI | 160 |
| MR Fiducial Coils | 5-10 |
| MR 2D image | 50 |
| US | 10-15 |

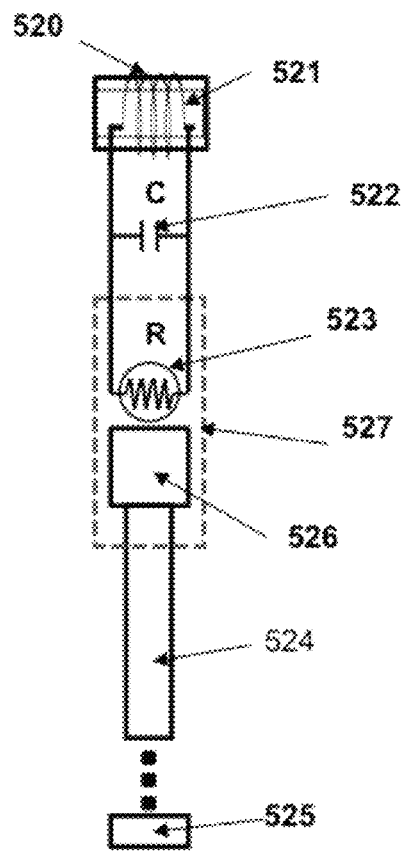
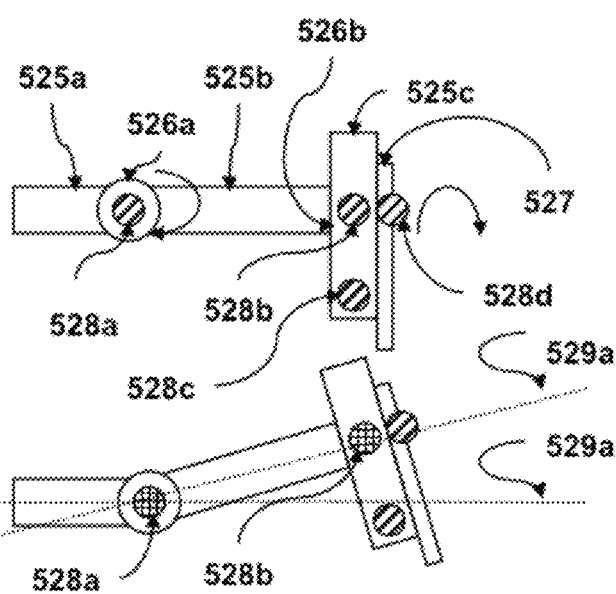
FIG. 5B
FIG. 5C
FIG. 5D

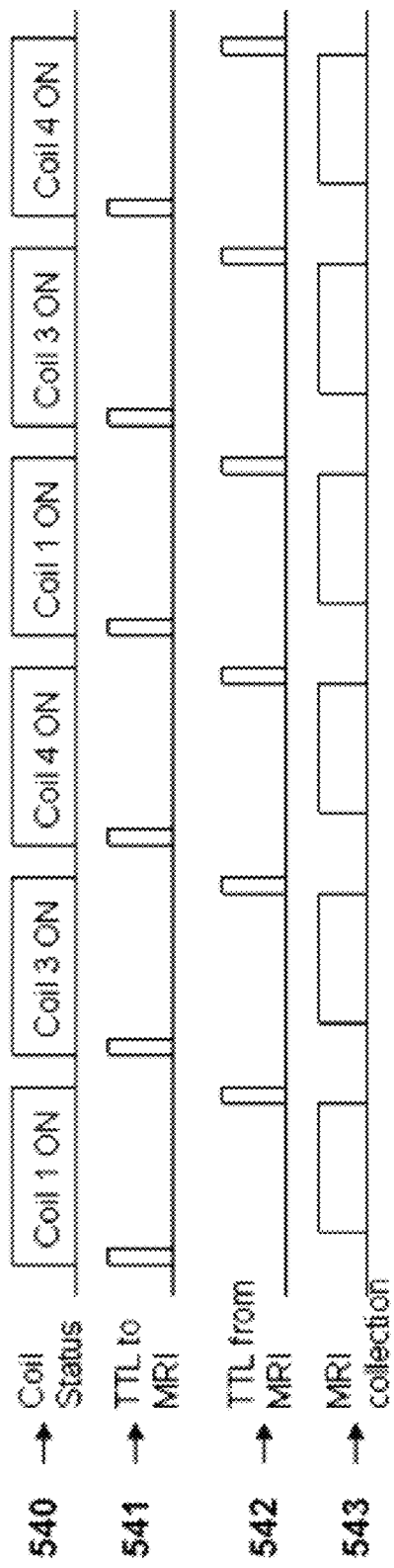

FIG. 9A
Intra-cardiac Access
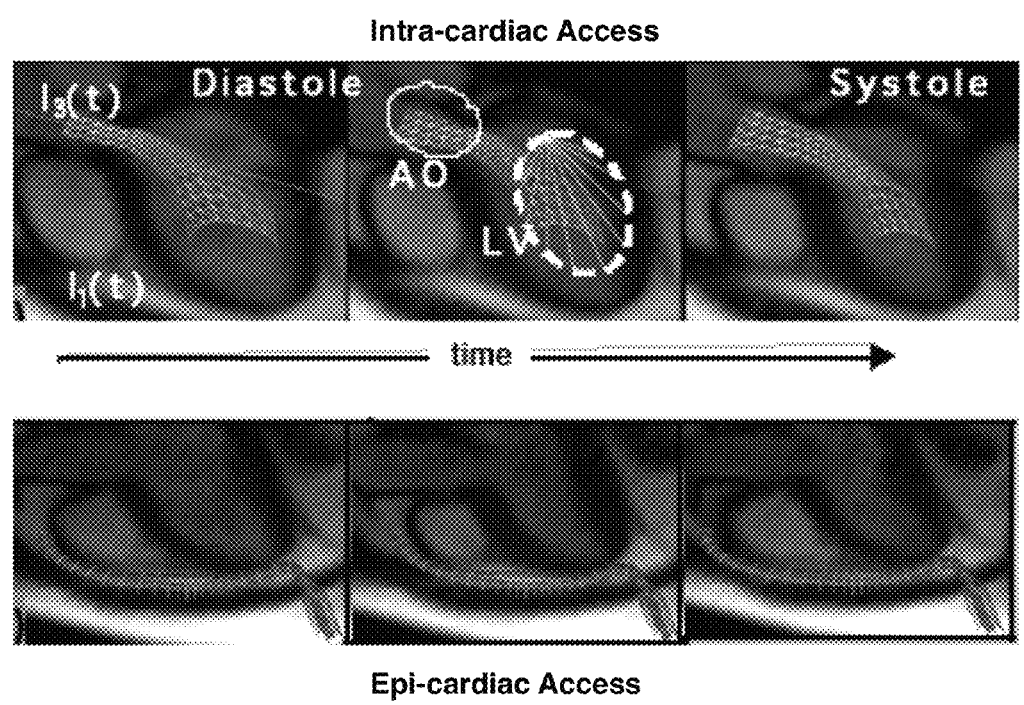
Epi-cardiac Access
FIG. 9B
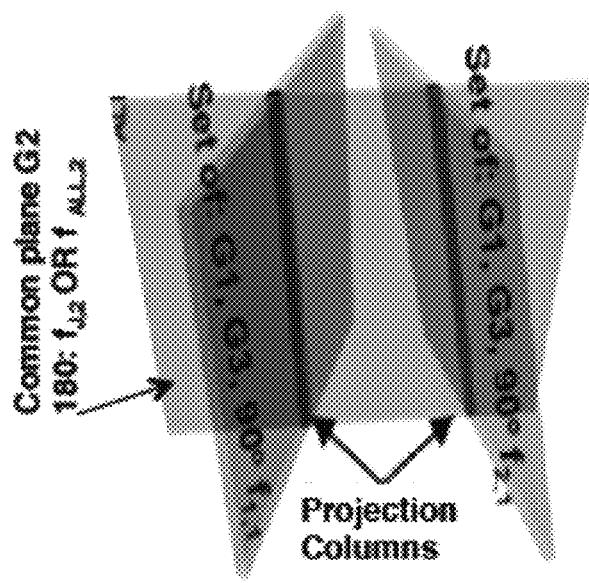
FIG. 10A

ROBOTIC DEVICE AND SYSTEM SOFTWARE, HARDWARE AND METHODS OF USE FOR IMAGE-GUIDED AND ROBOT-ASSISTED SURGERY

FEDERAL FUNDING LEGEND

This invention was made with governmental support under Grant Number 0932272 awarded by the National Science Foundation. The government has certain rights in the invention.

CROSS-REFERENCE TO RELATED APPLICATIONS

This application is a non-provisional under 35 U.S.C. §119(e) of provisional application U.S. Ser. No. 61/693,634, now abandoned, the entirety of which is hereby incorporated by reference.

BACKGROUND OF THE INVENTION

Field of the Invention

The present invention relates to the fields of robotics, robot assisted surgical procedures and software for the practice thereof. Specifically, the present invention provides a robotic system, including a robotic manipulator and actuator and applicable software and hardware, comprising a MRI-compatible medical robotic platform for in situ, real time image-guided diagnosis, surgeries and minimally invasive medical interventions.

Description of the Related Art

Robotic assistance in minimally invasive procedures, including Single Port Access (SPA) surgeries and percutaneous interventions, is emerging as a more patient-friendly, practice-enhancing and, eventually, cost-effective alternative to traditional open surgeries or free-hand interventions. New technologies achieve increasing levels of safety and functionality and new generations of physicians are better accustomed to computer-enabled tools than their predecessors. Such a paradigm shift requires robust, scalable and efficient methodology for integrating multimodal sensing, e.g., tissue and molecular level imaging, controlled systems such as robots and haptic devices, and, for example, the surgical, radiological, cardiological, etc. interventionalist. Major efforts by pioneering groups in developing innovative computational methods, robotic manipulators and haptic interfaces have paved the way toward this quantum leap. Looking into the future of image guided and robot-assisted (IGRA) procedures, several factors may contribute to next-generation systems, including the seamless integration of real-time image guidance that can locally assess the tissue pathology and function, with efficient operator interfacing.

Real-Time Image Guidance (RTIG) offers unique features for assessing the Area of Procedure (AoP), including 1) assessing real-time tissue deformation and motion, secondary to the procedure or natural motion, e.g. breathing or heart beating; 2) monitoring the tool(s) in 3D; and 3) updating the pathophysiology information of the targeted tissue. Endowed with such features, RTIG may facilitate a paradigm shift and methodological leap from current approaches of "keyhole" visualization, i.e. endoscopy or laparoscopy, and pre-operative imaging guidance, to a more global and informational-rich perception of the AoP, which can enable a wider range and levels of complex surgeries. Within this context, extensive groundbreaking work has been performed with different imaging modalities, including ultrasound (US), and magnetic resonance imaging (MRI), for free-hand or robot-assisted procedures.

IGRA procedures are challenging, highly complex and a wide range of clinical paradigms and enabling technologies have been or are currently pursued by many groups. Several IGRA devices have been developed or are under development. The MR-compatible NeuroArm, which may revolutionize MRI-guided surgeries, is a complex and high-cost technology, but it is unsuitable for real-time MR guidance. Another system, studied at the National Institutes of Health, is based on the Innomotion® robot, which is no longer offered commercially.

Thus, there is a recognized need in the art for improved image-guided and robot assisted procedures, particularly for real-time multimodality imaging for robot control and HIMI for man-in-the-loop autonomous or manual control of the robot. More specifically, the prior art is deficient in software and implementation systems to operate and guide robotic devices, systems that are designed for operation within the space constraints of imaging scanners, means for actuating the robotic than can perform in the very high magnetic field of a magnetic resonance environment and enable real-time tracking of tissue. The present invention fulfills this long-standing need and desire in the art.

SUMMARY OF THE INVENTION

The present invention is directed to a computer system for in-situ real time imaging guidance of a robot during a surgical procedure. The computer system comprises, in at least one computer having a memory, a processor and at least one network connection a plurality of modules configured to intraoperatively link an imaging modality, a medical robot and an operator thereof via a plurality of interfaces linking the same. The present invention is directed to a related computer system that comprises module configured to 1) control the imaging modality during the surgical procedure; 2) track a robot or interventional tools co-registered therewith; 3) track a tissue of interest; 4) process data acquired from the imaging modality and from the robot; 5) generate dynamic paths or corridors for safe and accurate motion of the robot outside and inside a patient's body; 6) visualize the robot and an area of procedure generated from the acquired data; and 7) utilize a force-feedback or haptic device to enable a human-machine interface. The present invention is directed another related computer system that further comprises a module configured to co-register a plurality of multimodal sensors with the robot and the imaging modality.

The present invention also is directed to a computer-implemented method for in-situ real time imaging guidance of a robot during a surgical procedure. The method comprises the steps of, intraoperatively in the computer system described herein, processing data to obtain a current status of a tissue and of the medical robot. generating at least one tissue boundary comprising an area of procedure or an area proximate to the access path of the robot or both is generated and the motion of the tissue boundary over the area of procedure is monitored dynamically. A position of the robot or an interventional tool comprising the same is tracked in reference to the area of procedure and based on individual visibilities of a plurality of markers disposed proximate to the robot and coupled to the imaging modality. The present invention is directed to a related method further comprising the step of producing a visualization of the area of procedure and the robot for the operator of the system as they are monitored and tracked. The present invention is directed to another related method further comprising the step of generating a view of the area of the procedure from one or more of a plurality of multimodal sensors co-registered with the robot and with a coordinate system of the imaging modality.

The present invention is directed further to a magnetic resonance image-guided and robot-assisted surgical system. The system comprises at least one computer processor, at least one computer memory, one or more robotic structures comprising a system registrable robot or interventional tools comprising the same, a magnetic resonance scanner registered with the robot, and a plurality of modules configured for on-the-fly operation with the computer processor and memory. The plurality of modules enable processor-executable instructions to 1) describe all MR-generated data about the robot and a tissue of interest in a patient, 2) establish a tissue boundary in an area of procedure, 3) dynamically monitor motion of the tissue boundary via the MR scanner or via one or more multimodal sensors comprising the robot and disposed inside or outside a patient's body, 4) track a location of the robot in reference to the area of procedure, 5) transmit the generated data to an operator of the system, 6) generate instructions for robot control and tracking from the generated data, 7) generate a view of the area of procedure and the robot during the surgical procedure for the operator, and 8) establish a plurality of interfaces among the robot, the scanner, the modules and the operator. The present invention is directed to a related magnetic resonance image-guided and robot-assisted surgical system wherein the plurality of modules are further configured to enable processor-executable instructions to generate and visualize a 4D view of the area of the procedure from data acquired via the multi-modal sensors. The present invention is directed to another related magnetic resonance image-guided and robot-assisted surgical system wherein the plurality of modules are further configured to enable processor-executable instructions to generate at least one signal intensity projection to monitor tissue-to-tissue or tissue-to-robot boundaries. The present invention is directed to yet another related magnetic resonance image-guided and robot-assisted surgical system wherein the plurality of modules are further configured to image natural tubular structures comprising the patient's body and artificial tubular structures comprising the robot or interventional tools.

The present invention is directed further still to non-transitory computer-readable data storage media and computer program product tangibly embodying the same storing computer-executable instructions that, when executed, perform actions in a computing system that enable the computer-implements methods described herein or store computer-executable instructions comprising the plurality of modules described herein.

Other and further aspects, features and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and, therefore, are not to be considered limiting in their scope.

FIGS. 5A-5L illustrate tracking a robot with MR fiducial markers.

FIGS. 9A-9B illustrate the output of the dedicated imaging thread that generates 4D Access Conduits from real-time oblique-to-each-other MRI slices for intra-cardial (FIG. 9A) and epi-cardial access (FIG. 9B).

FIG. 10A-10C depict MR pulse sequences for collection of multiple projection columns to generate the access corridors. FIG. 10A illustrates 3D selection of two projection columns that share a common imaging plane. FIG. 10B illustrates individual selection of each column. FIG. 10C illustrates the selection of two columns, with a common plane along axis G2, together via a single repetition for faster data collection.

FIG. 13A shows an original dynamic MR image collected with a speed of 50 ms/image, with a projection line (dashed) and the width of the area that the signal s integrated (solid box). FIG. 13B shows a graph of the signal with the LV and the two deeps left/right that correspond to myocardium.

FIGS. 20A and 20C show the specific implementation of the RF pulses, gradients and data acquisition waveforms and FIGS. 20B and 20D show the coverage of the corresponding k-space trajectories.

DESCRIPTION OF THE PREFERRED EMBODIMENTS

Figure 1:
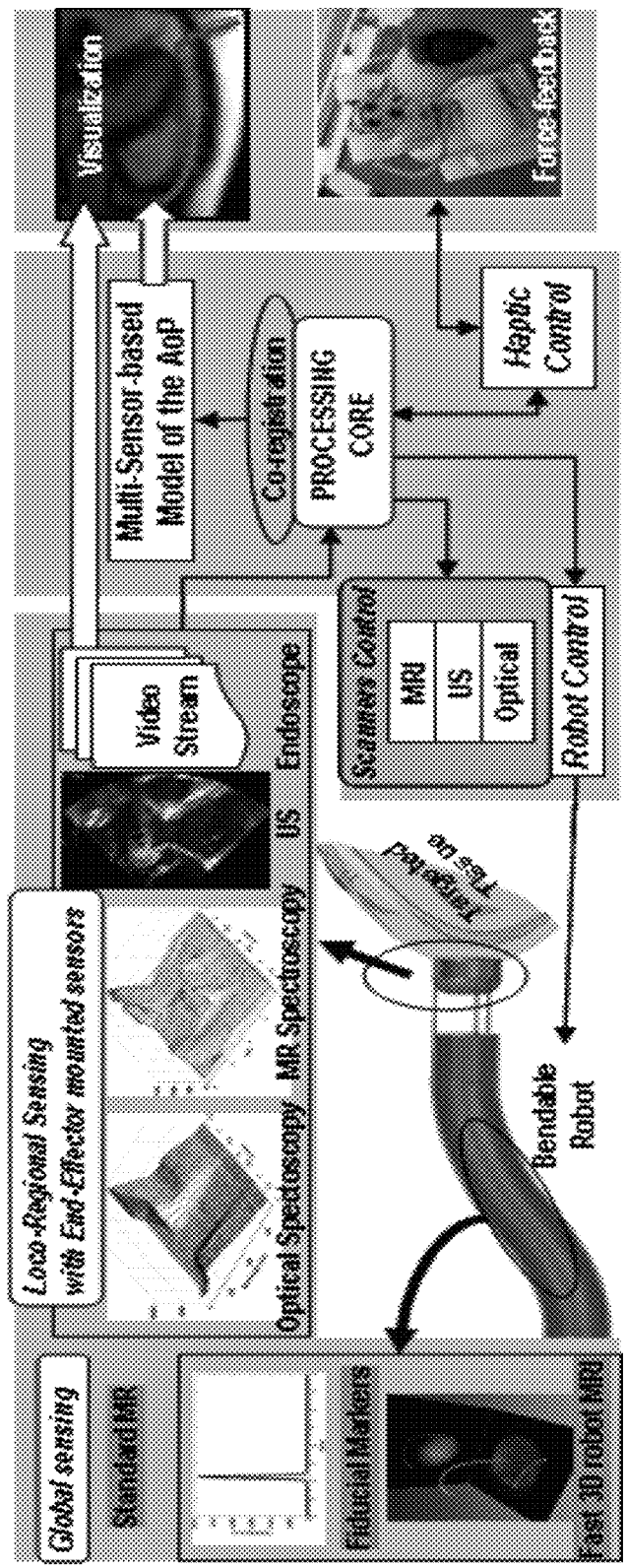
FIG. 1 is an Illustration of the general purpose medical robotic platform.

As used herein, the term "a" or "an", when used in conjunction with the term "comprising" in the claims and/or the specification, may refer to "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

As used herein, the term "or" in the claims refers to "and/or" unless explicitly indicated to refer to alternatives only or the alternatives are mutually exclusive, although the disclosure supports a definition that refers to only alternatives and "and/or."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the terms "computer" refers to one or more machines that comprise at least a memory, a processor and at least one wired and/or wireless network connection. A computer may comprise a desktop or laptop machine or other electronic media, for example, a smartphone or tablet, as are standard and currently known in the art. Without being limiting, any software, modules, applications, add-ons, plug-ins, programs and/or databases, etc. necessary for implementation of, but not limited to, the robot system, including the robotic manipulator, robotic sensors, etc., may be programmed into one or more computers, may be retrieved over the network connection or may be retrieved from a media storage device tangibly storing the same, may be tangibly stored in computer memory or other electronic media memory and are executable by the processor.

As used herein, the terms "robot" or "robotic manipulator" interchangeably refer to the remotely actuated manipulator for performing, for example, but not limited to, manipulator-assisted surgical, minimally invasive surgical and interventional diagnostic or therapeutic or a combination of diagnostic and therapeutic procedures, as described herein.

As used herein, the term "patient" refers to any mammal, preferably a human, that is the subject of a surgical procedure, surgery or minimally invasive procedure utilizing the image-guided robotic device and system described herein.

In one embodiment of the present invention there is provided computer system for in-situ real time imaging guidance of a robot during a surgical procedure, comprising, in at least one computer having a memory, a processor and at least one network connection: a plurality of modules configured to intraoperatively link an imaging modality, a medical robot and an operator thereof via a plurality of interfaces linking the same.

In this embodiment the plurality of modules may comprise at least a module configured to control the imaging modality during the surgical procedure; a module configured to track a robot or interventional tools co-registered therewith; a module configured to track a tissue of interest; a module configured to process data acquired from the imaging modality and from the robot; a module configured to generate dynamic paths or corridors for safe and accurate motion of the robot outside and inside a patient's body; a module configured to visualize the robot and an area of procedure generated from the acquired data; and a module configured to utilize a force-feedback or haptic device to enable a human-machine interface. Further to this embodiment the computer system may comprise a module configured to co-register a plurality of multimodal sensors with the robot and the imaging modality.

In one aspect of both embodiment the imaging modality control module may enable, during the surgical procedure, processor-executable instructions to: process data about a status of the tissue and of the robot; calculate changes thereto; identify events that trigger a change in data acquisition; select a response to the event and devise an image acquisition strategy based thereon; and transmit the image acquisition strategy to the imaging modality. In this aspect triggering events may be identified via instructions to compare the changes to a list of range-of-form values algorithmically.

In another aspect the tissue tracking module enables processor-executable instructions to: select imaging sequences with the imaging modality and set parameters to generate contrast differences within the tissue; generate at least one observable tissue boundary of interest from one or more signal intensity or image projections obtained during imaging; and dynamically monitor motion of the tissue boundary during the surgical procedure. In this aspect the tissue boundary may comprise a boundary around the tissue in an area of procedure or a boundary around tissue proximate to an access path of the medical robot or both. Further to this aspect tissue the tracking module may enable further processor-executable instructions to infuse an exogenous contrast agent into the tissue prior to or during the select instruction.

In yet another aspect the robot tracking module may enable processor-executable instructions to detect one or more of a plurality of markers disposed proximate to the robot and coupled to the imaging modality; and to extract coordinates of the markers relative to a coordinate system of the imaging modality to determine location of the robot;

In yet another aspect the visualization module may enable processor-executable instructions to detect only a single marker location for each localization step for the robot.

In all embodiments and aspects thereof one of the plurality of interfaces may enable manual control by the operator of the medical robot and the imaging modality. Also, the plurality of modules may operate on-the-fly. In addition the imaging modality is magnetic resonance imaging or spectroscopy or a combination thereof, ultrasound imaging, x-ray computed tomography, x-ray mammography, optical imaging, or video.

In another embodiment of the present invention there is provided a computer-implemented method for in-situ real time imaging guidance of a robot during a surgical procedure, comprising the steps of, intraoperatively in the computer system as described supra, processing data to obtain a current status of a tissue and of the medical robot; generating at least one tissue boundary comprising an area of procedure or an area proximate to the access path of the robot or both; dynamically monitoring motion of the tissue boundary over the area of procedure; and tracking a position of the robot or an interventional tool comprising the same in reference to the area of procedure based on individual visibilities of a plurality of markers disposed proximate to the robot and coupled to the imaging modality.

Further to this embodiment the method may comprise producing a visualization of the area of procedure and the robot for the operator of the system as they are monitored and tracked. In this further embodiment the visualization may comprise a visual image, a model, a virtual reality scene, an enhanced reality scene or a superimposition or combination thereof. In another further embodiment the method may comprise generating a view of the area of the procedure from one or more of a plurality of multimodal sensors co-registered with the robot and with a coordinate system of the imaging modality.

In an aspect of these embodiments the processing step may comprise calculating changes to the status of the tissue and robot; identifying events that trigger a change in data acquisition; comparing, algorithmically, the change to a list of range-of-form values; selecting a response to the event based on a comparison of the values; and devising an image acquisition strategy based on the response which is transmitted to the imaging modality. In this aspect the method may further comprise infusing an exogenous contrast agent into the tissue prior to or during generating the tissue boundary.

In another aspect the tracking step may comprises extracting coordinates of the markers onto the robot or the interventional tool relative to a coordinate system of the imaging modality to detect a location thereof during a localization step; wherein only a single marker location is detected for a localization step during robot tracking. In this aspect only a single marker location may be detected for the localization step.

In yet another embodiment of the present invention there is provided a non-transitory computer-readable data storage medium storing computer-executable instructions that, when executed, perform actions in a computing system that enable the computer-implemented method steps described supra. In a related embodiment there is provided computer program product, tangibly embodied in the non-transitory computer readable medium.

In yet another embodiment of the present invention there is provided a magnetic resonance image-guided and robot-assisted surgical system, comprising at least one computer processor; at least one computer memory; one or more robotic structures comprising a system registrable robot or interventional tools comprising the same; a magnetic resonance scanner registered with the robot; a plurality of modules configured for on-the-fly operation with the computer processor and memory that enable processor-executable instructions to: describe all MR-generated data about the robot and a tissue of interest in a patient; establish a tissue boundary in an area of procedure; dynamically monitor motion of the tissue boundary via the MR scanner or via one or more multimodal sensors comprising the robot and disposed inside or outside a patient's body; track a location of the robot in reference to the area of procedure; transmit the generated data to an operator of the system; generate instructions for robot control and tracking from the generated data; generate a view of the area of procedure and the robot during the surgical procedure for the operator; and establish a plurality of interfaces among the robot, the scanner, the modules and the operator.

Further to this embodiment the plurality of modules may be configured to enable processor-executable instructions to generate and visualize a 4D view of the area of the procedure from data acquired via the multi-modal sensors. In this further embodiment multi-modal sensors may be co-registered with a coordinate system comprising the magnetic resonance scanner. In another further embodiment the plurality of modules may be further configured to enable processor-executable instructions to generate at least one signal intensity projection to monitor tissue-to-tissue or tissue-to-robot boundaries. Further still the plurality of modules may be configured to image natural tubular structures comprising the patient's body and artificial tubular structures comprising the robot or interventional tools. In this further embodiment the instructions to image natural and artificial tubular structures operate to infuse or load a contrast agent into the structure; acquire at least one 2D projection of a 3D volume that contains the structure with contrast agent; and generate a 3D image from the 2D projections. Particularly, when at least two 2D projections are acquired, the projections may be at any angle relative one to another. Also, a selected order of radiofrequency pulses and magnetic field gradient pulses used to acquire the 2D projection at least reduces a signal from non-contrasted structures. In all these embodiments at least one of the plurality of interfaces enables manual control by the operator of the robot and the MR scanner.

In an aspect of this embodiment the instructions to describe all MR-generated data may operate to process data about a status of the tissue and of the robot; calculate changes thereto; identify, algorithmically, events that trigger a change in data acquisition via instructions to compare the changes to a list of range-of-form values; select a response to the event and devise an MR image acquisition strategy based thereon; and transmit the MR image acquisition strategy to the MR scanner.

In another aspect the instructions to establish a tissue boundary may operate to infuse, optionally, an exogenous contrast agent into the tissue, if required; select MR imaging sequences and set parameters to generate contrast differences within the tissue; and generate the tissue boundary from one or more image projections obtained during magnetic resonance imaging.

In yet another aspect the instructions to track a location of the robot may operate to track a position of the robot in reference to the area of procedure based on an on/off status of a plurality of markers disposed proximate thereto and co-registered with a coordinate system of the MR scanner; and apply motion filtering to constrain robot motion. In this aspect the instructions to track a position of the robot may operate to extract coordinates of the plurality of markers relative to the coordinate system of the MR scanner to detect locations thereof; wherein only a single marker location is detected for a localization step during robot tracking.

In yet another aspect the instructions to generate at least one signal intensity operate to excite the tissue contained in at least a 3D column along a selected direction of the projection via radiofrequency pulsing; and manipulate a magnetic field gradient; acquire raw data from the MR scanner; and generate a 1D projection of the signal intensity from the raw data. In this aspect if more than one 3D column comprises a plane, the module enables instructions to send a plurality of radiofrequency pulse thereby increasing the rate of acquisition.

In yet another aspect the instructions for robot control may operate to enable manual operator and automated control of the robot for acquisition of the 2D projections under MR image-guidance. In this aspect the instructions for robot control particularly may operate to, via manual operator control, select at least one plane, at least one projection axis and at projection wide; and select, concomitantly, 3D projection columns and group the same; and, via automatic control, may operate to calculate magnetic resonance acquisition parameters comprising a pulse gradient and gradient strength; and, sequentially, update the acquisition parameters; acquire, dynamically, and analyze the projections; and generate a dynamic tissue model; and then to calculate a dynamic corridor and trajectory by which to control the robot; calculate a dynamic rendering of a haptic device; and produce an augmented reality of image guidance therefrom.

In yet another embodiment of the present invention there is provided a non-transitory computer-readable data storage medium storing computer-executable instructions comprising the plurality of modules described supra. In a related embodiment there is provided computer program product, tangibly embodied in the non-transitory computer readable medium.

Provided herein is real-time tracking of surgical tools with multiple MR-visible markers that can be positioned onto the surgical tool for tracking the tool itself. Also provided is the real-time tracking of tissue, with a method that collects multiple projections with specialized MRI data collection protocols, i.e. pulse sequences, for monitoring the motion of tissue for use in both diagnostic practices and in surgical procedures. The method can theoretically allow the collection of projections every 3-4 ms allowing the monitoring of the motion of multiple sites.

Also provided are related methods for automated guidance and maneuvering of surgical robots and for directing manual maneuvering of the robots via specialized haptic devices that use MR data instead of force sensors. Robot-mounted loco-regional biosensing uses a combination of optical and ultrasound methods as described herein. Ultra-fast 3D/volumetric MRI imaging of a bendable surgical tool is enabled.

In addition software enabling the methods and procedures described herein is provide, for example, software for the control of the collection of the MR data and for the reconstruction of the raw data collected from methods described supra and for the generation of a realistic virtual environment, based on real-data and no modeling, for visualizing and guiding a surgery. Furthermore there is provided software for processing and utilizing image modality-extracted information useful for the autonomous or semi-autonomous control of the robot and for interfacing the operator to the robot and the area of operation in general by an "expert-like" advising of the operator via a haptic or force-feedback device.

As such, the present invention provides a general-purpose versatile medical robotic platform and software system. The system comprises a modality-independent robust platform such that methodologies for collecting, fusing and presenting raw data are reconfigurable for different current and emerging medical modalities. The system utilizes real and real-time data and minimizes parametric and/or abstracted assumptions about the environment, thereby enabling in-situ real-time imaging guidance. Multi-modal sensing is implemented by incorporating imaging sensors on the robot and using the robot actuation for generating multimodal spatio-temporal data that is inherently co-registered.

More specifically, the system utilizes MRI data collection strategies that translate raw images to decision-making via methods for cross-modality data interpretation and event-based characterization. The system provides enhancement of low informational content intra-operative dynamic data from high informational content pre-operative data, thereby enabling collection of all needed information to plan and guide a procedure. As such, the system comprises a computational core that generates and integrates image-based information that explicitly represents and considers physical or environmental factors. Also provided are interfaces that render multi-modal data, provide comprehensive perception of the environment and achieve human- or man-in-the-loop control with minimal effort and distraction for the human operator.

In a preferred embodiment there is provided a robotic platform for general medical use. The platform comprises a general purpose, bendable robotic manipulator that conforms to the access of area of the procedure. The manipulator must be modular and reconfigurable, applicable to a wide range of operational and application scenarios and can form the base for a fundamental framework upon which other systems can be built.

The medical platform also comprises robot control methods based on information, which is extracted dynamically from real-time, multi-modal imaging. The data is collected by an array of sensors at the robot end-effector and distributed onto its body for safely and accurately maneuvering within dynamically changing environments. This enables direct and intuitive viewing of the AoP by the operator, while minimizing run-time modeling, assumptions, and computational layers.

The medical platform further comprises intra-operative, robot-assisted, on-line diagnosis tools using the robot as a sensor-suite for assessing pathophysiologic signatures that can guide the procedure and assess its results. Beyond traditional imaging, such as MRI and US, the sensors are configured to interrogate molecular features of the tissue in situ. The robot comprises a smart-sensor platform configured to facilitate spatio-temporal, multi-modal co-registration for fine control and fusion for the interface with the human operator.

As described below, the invention provides a number of advantages and uses, however such advantages and uses are not limited by such description. Embodiments of the present invention are better illustrated with reference to the FIG. (s), however, such reference is not meant to limit the present invention in any fashion. The embodiments and variations described in detail herein are to be interpreted by the appended claims and equivalents thereof.

FIG. 1 illustrates that multi-modal sensing occurs, e.g., with MRI, at the global level for robot control and at the regional level with robot-carried sensors, e.g., MR, US, or optical, for sensing at the molecular level. All modalities are inherently co-registered to the coordinate system of the MR scanner simplifying robot control, multi-modal data fusion and visual/FFI. Table 1 illustrates intra-operative global tracking and local tissue pathology.

TABLE 1

| GLOBAL | Method | Speed (ms) |
| --- | --- | --- |
| Track points | Fiducial RF coils | 5-7/marker |
| Track robot shaft | 2D Thick slap MPI | 50-80/projection |
| Tissue imaging | Collaborative | ≥50/slice |
| Track tissue bands | 1D projections | 5-10/projection |
| LOCAL | | |
| MR spectroscopy | End-effector mounted RF coil | |
| US & agent activation | End-effector mounted US probe | |
| Optical spectroscopy | End-effector mounted optical LIF probe | |

In another preferred embodiment, there are provided methods for robot control and procedure guidance with intra-operative real-time imaging. In a non-limiting example, MRI is utilized for tracking the robot and viewing the AoP. MRI offers many soft-tissue contrast mechanisms for assessing anatomy and function. MRI enables utilization of visualizing and tracking tools and robotic manipulators. MRI is a true 3D or multi-slice imaging and enables on-the-fly adjustment of the acquisition parameters, including the orientation of imaging plane(s) from the robotic control core. MRI has operator-independent performance compared to ultrasound. MRI operates without ionizing radiation as compared to X-rays. Most particularly, MRI exhibits a unique feature in that the robot can be registered to the inherent coordinate system of the MR scanner.

As provided herein, intra-operative real-time imaging is expanded in two directions. Firstly, estimations, models or assumptions based on prior data are minimized. Secondly, computational layers between the operator and the patient are minimized. This increases the confidence of medical operators in robotic technology and minimizes potential areas of malfunction that may harm the subject.

In one aspect of this preferred embodiment there is provided intra-operative holonomic modeling for IGRA procedures. In this aspect two complementary MR methods are integrated. The first is 3D imaging of the robot utilizing image reconstruction from multiple thick-slab projections. The second method utilizes MR fiducial markers on the robot for continuous tracking inside the patient at 200 Hz/marker. In a related aspect, there are provided algorithms configured to control the time instance for which each measurement is performed to optimize speed of acquisition and information content.

In another aspect there is provided robot-facilitated sensing that bridges molecular and macroscopic levels of imaging with guidance thereby providing an operator with means for assessing the pathology of tissue at the AoP on-the-fly. By using the end-effector for carrying and manipulating the spatio-temporal scanning of high-specificity sensors, loco-regional sensing of the AoP is enabled. For example, the end-effector may carry optical sensors for LIF and/or a MR RF coil for local MRS. This enables mechanical coupling of tissue (MRI) and molecular (LIF and MRS) level modalities for in situ probing of the AoP and inherent co-registration at the level of data collection, unlike computationally expensive post-processing. These aspects bring high-specificity biosensing to the AoP.

Figure 2:
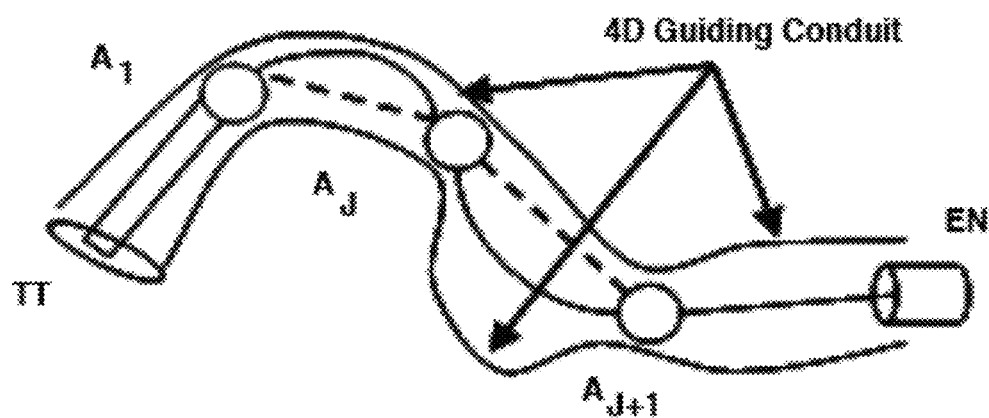
FIG. 2 is a cartoon representation of a single port access (SPA) surgery.

In yet another preferred embodiment there is provided a framework comprising a robotic platform and generalized intra-operative image-based control configured for use with current and future versions of endoscopic procedures, such as, but not limited to, image-guided natural orifice transluminal endoscopic surgery (NOTES) of image-guided NOTES or other single port access (SPA) surgeries. The framework comprises robotic structures or articulated structures that are deployed by nodes through 4D guiding conduits. The nodes carry MR fiducial markers the positions of which are adjusted in response to the constraints imposed by the 4D guiding conduit. The guiding conduits are 4D virtual structures that change to adjust to the transient condition of the tissue that surrounds them. For example, as depicted in FIG. 2, a SPA procedure can be tasked with maneuvering a tubular steerable device from an initial location EN, i.e., a percutaneous port or a natural orifice, to a target TT via a conduit that is a spatio-temporal tube-like virtual entity.

In yet another preferred embodiment there is provided a human-information/machine interface (HIMI). The HIMI is a dual visual (VI) and force-feedback interface (FFI) that immerses the operator in information, i.e., data hierarchically matured to procedure-related information, and facilitates image-based, man-in-the-loop control. For the operator the HIMI provides a fast learning curve and intuitiveness with no distractions or additional workloads for using the same.

Figure 3A:
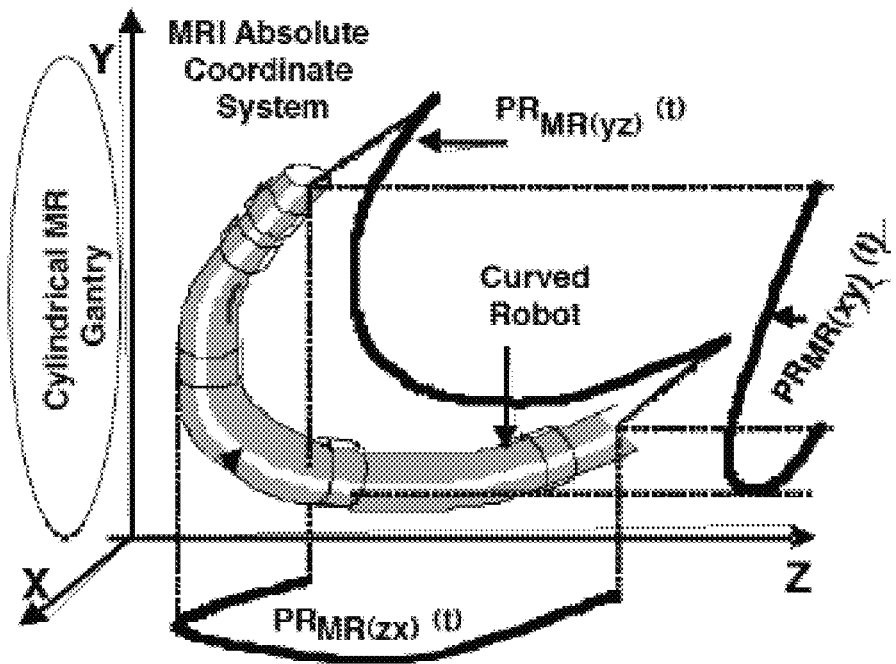
FIGS. 3A-3B are an overview of intra-operative robot detection and tracking methods (FIG. 3A) and a flowchart for the generation of the robot model (FIG. 3B).
Figure 3B:
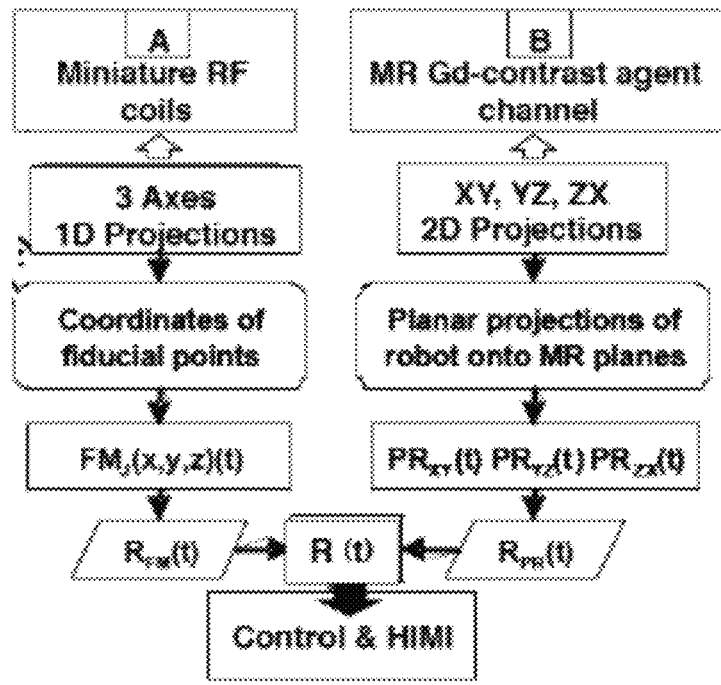

In yet another preferred embodiment there are provided methods for multimodal intra-operative sensing. This enables the integration of MR methods for the collection of complementary spatio-temporal information, which when combined, offers a 4D view of the AoP. This view is used by the autonomous or human-guided robot control. It is contemplated that this approach enables medical robotic tools to function as multi-tools instead of simply as applicators. These methods generate inherently co-registered, multi-modal data at the data-acquisition stage. The registration will be relative to the common MR coordinate system that addresses multi-modal co-registration in a straightforward way, eliminating any unnecessary complexity and assumptions. FIG. 3A provides an overview of methods for intra-operative detection and tracking of the robot in an MRI absolute co-ordinate system and FIG. 3B is a flowchart illustrating the generation of the robot depicted in FIG. 3A. The robot is a curved robot that comprises a plurality of miniature RF coils and has a MR gadolinium (Gd)-contrast agent channel. 2D XY-, YZ,- and ZX projections of the robot are depicted in the of the MR planes of the coordinate system.

Figure 4A:
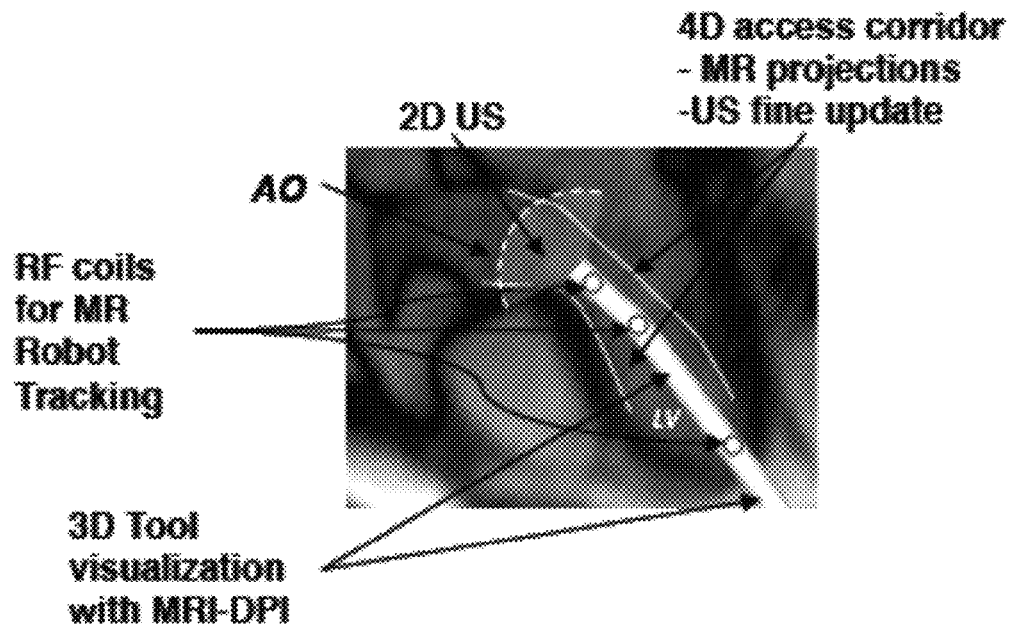
FIGS. 4A-4B depict MR and US methods (FIG. 4A) and illustrate interleaving (not in scale) (FIG. 4B) of these methods. Methods with (*) are started by the operator. The table lists estimated time per data set collection.
Figure 4B:
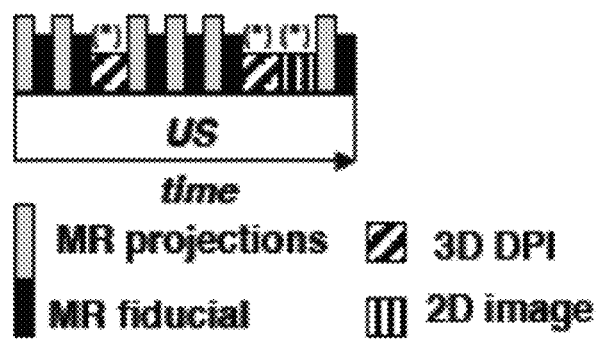

Moreover, as illustrated in FIG. 4A, multi-modality based robot control and HIMI with concurrent collection of intra-operative MR and robot-mounted US (RM-US) images. Multi-modality data is used for on-the-fly generation and update of a dynamic virtual model of the AoP, i.e. 4D spatiotemporal information, in the form of access corridors and guidance trajectories for robot control, as well as operator visuo-haptic interfacing. By combining the benefits of intra-operative MR and US to acquire complementary spatiotemporal information, the proposed approach will develop methods to create a dynamic model of the AoP as close to the real world as possible. As depicted in FIG. 4B, intra-operative MRI includes interleaved MR methods to track the moving endocardium, 3D imaging of the endo-patient portion of the robot, and tracking fiducial markers on the robot. Intra-operative RM-US will be performed concurrently with MRI to generate real-time images forward of the robot end-effector for guidance. Moreover, operator-triggered standard MR or US protocols can be interleaved with the methods provided herein to assess the performance of the procedure.

Figure 5A:
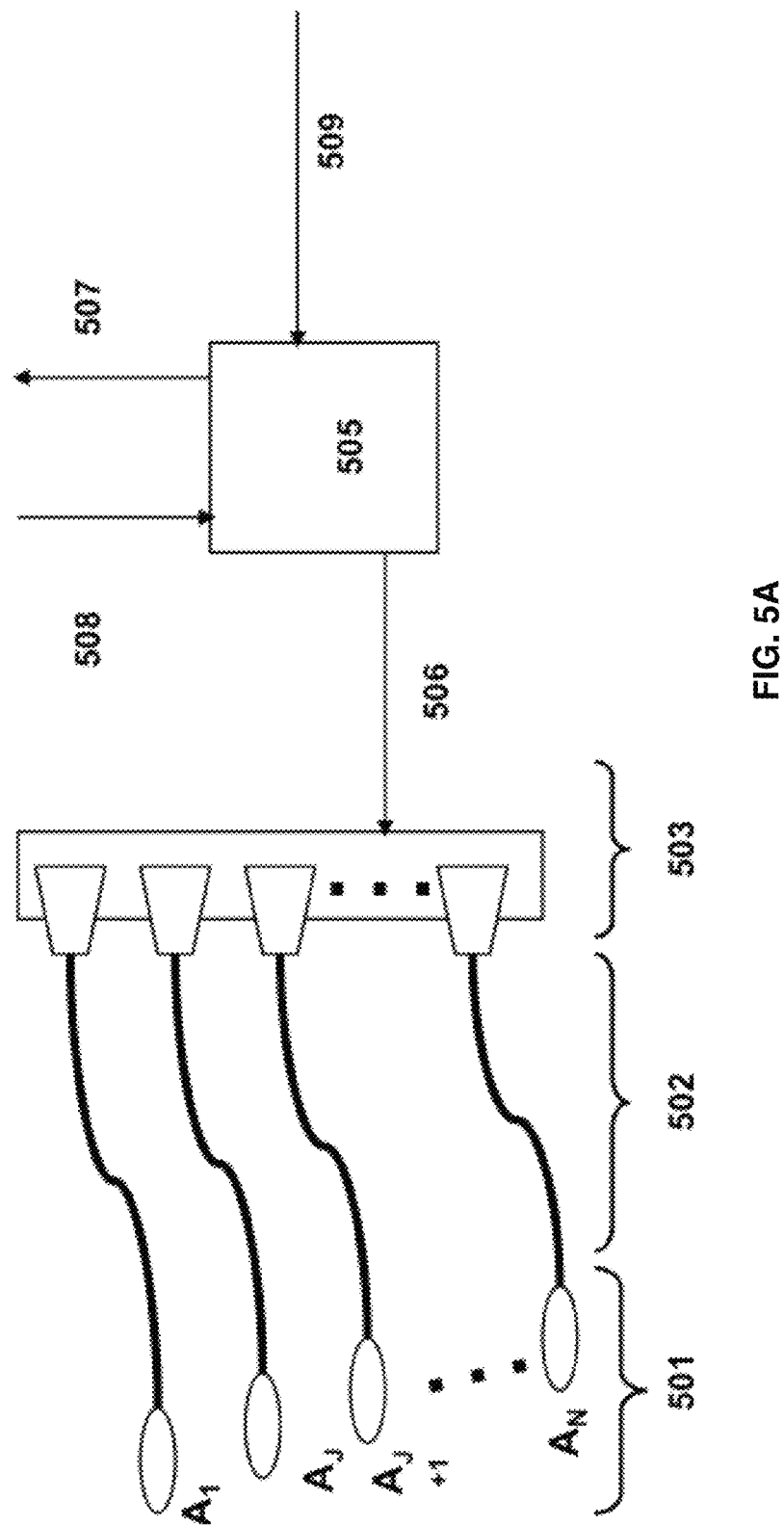
Figures 5E, 5F, 5G:
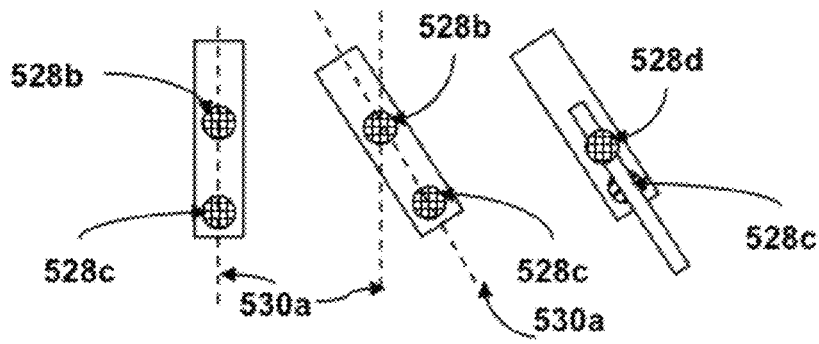

According to another embodiment, and in reference to FIG. 5A, a method is described for tracking a robot or interventional tools with MRI using a plurality of radiofrequency (RF) micro-coils that are inductively coupled to RF coils that are external to the patient and used to image the procedure. According to a preferred embodiment and in reference to FIG. 5A, a plurality of MR fiducial markers 501 have computer-controlled visibility, i.e. any one of them or any combination of them can turned ON, i.e., are MRI visible, or turned OFF, i.e., are MRI invisible, according to the particular needs for visualizing and tracking the entire or parts or points of the robot or the tool. The essence of selectively making MR visible one or a limited number of markers is that MR data collection and processing to extract the coordinates of the markers relative to the coordinate system of the MR scanner is substantially faster as compared to when all markers are active.

Measuring the position of these coils relative to the coordinate system of the MR scanner can be performed by 1) collecting projections along the three axes of the scanner as established by Dumoulin (1) and others (2-4) or 2) collecting fast MR images. In the absence of any other source of signal, a single coil will exhibit a peak along each projection at the position of the coil on the corresponding axis of the MR scanner in which localization is on the Z-axis with a 1.1-mm coil (5-7). To track a robot or tool, multiple micro-coils are needed to track multiple points on the tools or robot. However, when multiple passive markers are simultaneously used, it is not easy to identify which peak corresponds to which marker. To unambiguously distinguish the markers and to avoid a high number of acquisitions and/or post-processing (4), the computer-controlled selective visualization allows only one marker to be tuned for each localization step. The rest are detuned by a photoresistor or photodiode that receives light via optical fibers. It is noted that the employed inductively coupled coils operate with low excitation pulses transmitted by the scanner RF coils so the surrounding tissue is minimally excited reducing unwanted background signal.

In reference to FIG. 5B that shows one of such markers, the selective visibility of those markers is preferentially implemented by optically detune the tuning circuit of the RF coil 520. Each such marker comprising 1) an RF coil 520 that is made by winding appropriate wire in appropriate shape, such as but not limited to a solenoid, a sphere, a FIG. 8, 2) source 521 of MR signal that the coil 520 is wrapped around, example but not limited to is a vial or other container that contains MR signal source material such as a H (proton) signal source, 3) a tuning circuit with appropriate capacitance C 522, to tune the resonance frequency of the RF coil 520 to the operation frequency of the MR scanner, and a photoresistor or photodiode 523, and 4) an optical fiber 524 that its distal end is appropriately oriented to deliver light from a light source 503 onto the photoresistor or photodiode 523. The marker assembly, may farther require a lens 526 to better focus the light onto the photoresistor or photodiode, and appropriate coverage 627 to eliminate unwanted light, e.g. ambient light, to reach and activate the photoresistor or photodiode.

Also according to this embodiment and in reference to FIG. 5A, each one of the plurality of markers 501 is connected with a plurality of optical fibers 502 each one connected to one of a plurality of light sources 503 such as, but not limited to, light emission diodes (LED) that are part of a power supply and control circuit that is standard to the specialists in the art of electronics. The system further includes an electronic unit or a micro-controller or any general embedded system 505 that has the following functions: 1) receive commands or signals externally 509 that set the particular pattern to make MR visible and invisible any number or combination of the markers, with any desired order and duration, 2) control the MR visibility of each one of the plurality of light sources 503 via an appropriate control or circuit output 506 in order. This can be done, for example, but not limited to, turning the voltage high and low that is supplied to a particular LED), 3) if selected by the operator, send a triggering pulse, such as a TTL pulse, to the MR scanner in order to initiate an MR data collection session, 4) if selected by the operator, receive a triggering pulse, such as a TTL pulse, from the MR scanner that signals the termination of an MR data collection session so the unit proceeds to the next cycle.

According to another aspect of this embodiment and in reference to FIG. 5C-5H, the plurality of the markers are appropriately distributed on the structure of the robot or tool track and visualize the motion of the different actuated parts. As example, and in reference to FIG. 5C, for an articulated robot or tool, for each rotational or prismatic joint two such markers are needed one on each side of the joint, or on each one of the joint links. In the example shown in FIG. 5C, with the actuated articulated manipulator that is composed of three links 525a-c, two rotational joints 526a-b one orthogonal to each other, and one prismatic joint 527 that carries the interventional tool, four markers 528a-d are placed. In reference to FIGS. 5C and 5D, when joint 526a is actuated, then only markers 528a and 528b need to be visualized to monitor the angulation around this joint and calculating the angle between the dotted lines 529a and 529b. When joint 526b is actuated, I reference to FIGS. 5E and 5F, then only two markers needed 528b and 528c in order to monitor this rotation and calculate the angle between the dashed lines 530a and 530b. Alike, when the tool is extended with the prismatic joint 527, only two joints are needed 528d and 528c. This example further underscores the value of this embodiment since with appropriate placement and selection of the markers only a limited number is needed to be used and thus speeding up acquisition and thus speed of tracking the actuated part of the robot or tool.

Figure 5H:
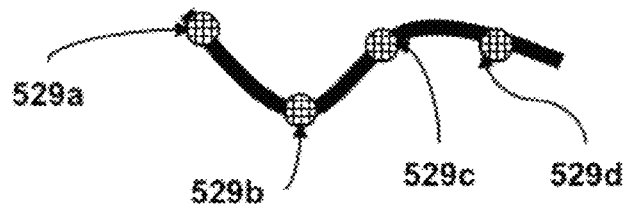

Another example in reference to FIG. 5H is this of curved tools, such as snake-like robots, that can be tracked with a limited number of markers 529a-d and known the position in space of those markers the shape of the tool can be reconstructed, as example by fitting the points of the markers with a spline function. At this case, each one of the markers is sequentially visualized, and if only part of the curved tool is actuated then only the markers on this part of the tool need to be tracked further speeding up tracking.

Figure 5I:
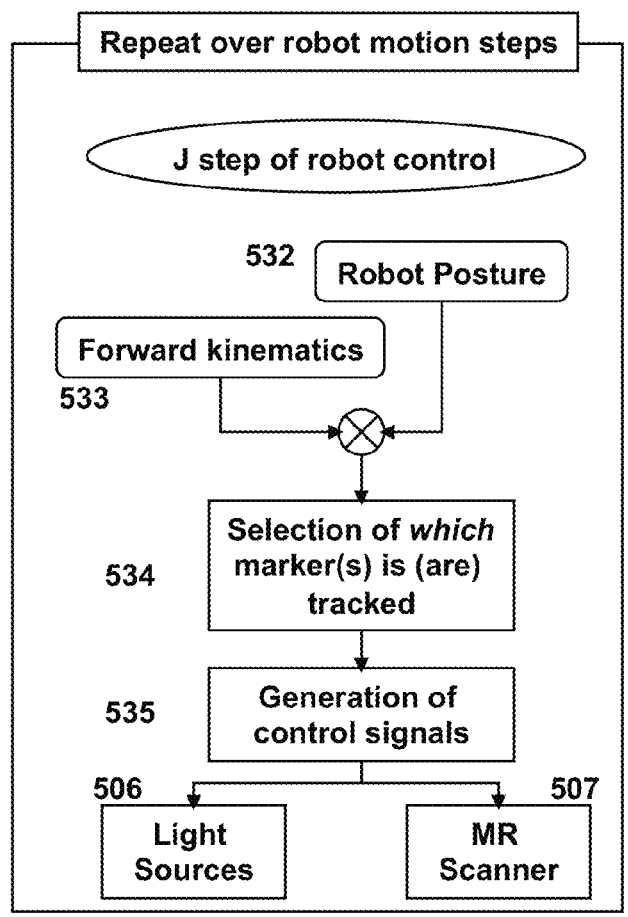

Another preferred aspect of this embodiment, is that only a limited number of the plurality of markers is selectively MR visible via the control of unit 505 and those markers are selected as to track only a specific portion of the robot or tool, as example but not limited to, when only a part of the robot or tool is actuated, for example, as shown in the sequence of FIGS. 5C-5G. Therefore, the microcontroller unit (505) or the processing unit that runs the robot control runs appropriate code that may, as example, have the structure shown in FIG. 5I) that entails the following aspects and processes: 1) for a robot motion step, say J, the robot posture 532 (i.e. coordinates of its joints and links relative to the MR scanner) and the forward kinematics 533, i.e. coordinates of its joints and links relative to the MR scanner after a command is executed) are used as input, 2) a process step 534 that analyzes those information and selects which markers need to be tracked in order to visualize the actuated portion of the robot or tool, 3) a process step 535 that determines the control signal 506 to the light sources 503 and the control signal 507 to the MR scanner.

Process step 535 may have the code structure described below in order to loop tracking through the markers that were selected by process 534, and tune/detune the corresponding RF coils.

```
Define Function COIL(J, K)
J = 1 to Maximum # of coils
K = 0 detuned
K = 1 tuned
Each coil has a flag CF(k): CF(k) = 1 if selected
One flag for SENT TTL
One flag for RECEIVE TTL
After pressing PREPARE
Calculate NCOILS =-sum{CF(k)}
Update the SetUp Screen
WHILE statement (until STOP pressed)
FOR J TO NCOILS
COIL(J,1) # set coil J to tune
COIL(L, 0) # set coils L <> J to detune
Delay(D1)
If SENT TTL flag = YES then Sent TTL to MRI
If RECEIVE TTL flag = YES Receive TTL from MRI
Set ALL coils to default
(e.g. is default is tuned then:
For m TO MAXCOILS
COIL(M,1)
)
Delay(D1)
NEXT J
END WHILE
```

FIG. 5J depicts a time-series control and events for a multi-coil tracking of a robot that uses 4 markers. In this instance a time-series is generated for sequentially tracking Coils 1, 3 and 4, while coil 2 is not MR visible. FIG. 5J depicts the time series, showing the coil status 540, the transistor-transistor logic (TTL) pulse to the MRI scanner 541 that is equivalent to control signal 507 in FIG. 5A, the TTL from the MRI 542, that is equivalent to control signal 508 in FIG. 5A, and the event of MR data collection, imaging or projections, 543 that occurs between the TTL pulses.

Furthermore, according to this embodiment, the above described controls of the markers can be automated, as described above in reference to FIG. 5I, or can be set manually by the operator via a graphical user interface (GUI). When the procedure is automated, the time-series of marker control, i.e. which markers are MR visible, for what duration and what order, can change on-the-fly by the control software of the robot. When the time series is set by the operator, the GUI allows presetting, by means of standard graphical and human interface devices, such as a mouse: 1) which markers will be MR visible, 2) in what order they will be turned MR visible/invisible (i.e. tuned/detuned), 3) any delays required for the system to eclectically/electronically settle, 4) whether a TTL trigger will be send to the MR scanner to initiate MR data acquisition, 5) whether a TTL trigger will be received from the MR scanner to trigger the tuning (or MR visibility) of the next RF coil, and 6) the number of the repetitions of the sequence or alternatively selection of a manual stop by means of a STOP button. The GUI may further have a RUN button to initiate the execution of the preset time series.

Figure 5K:
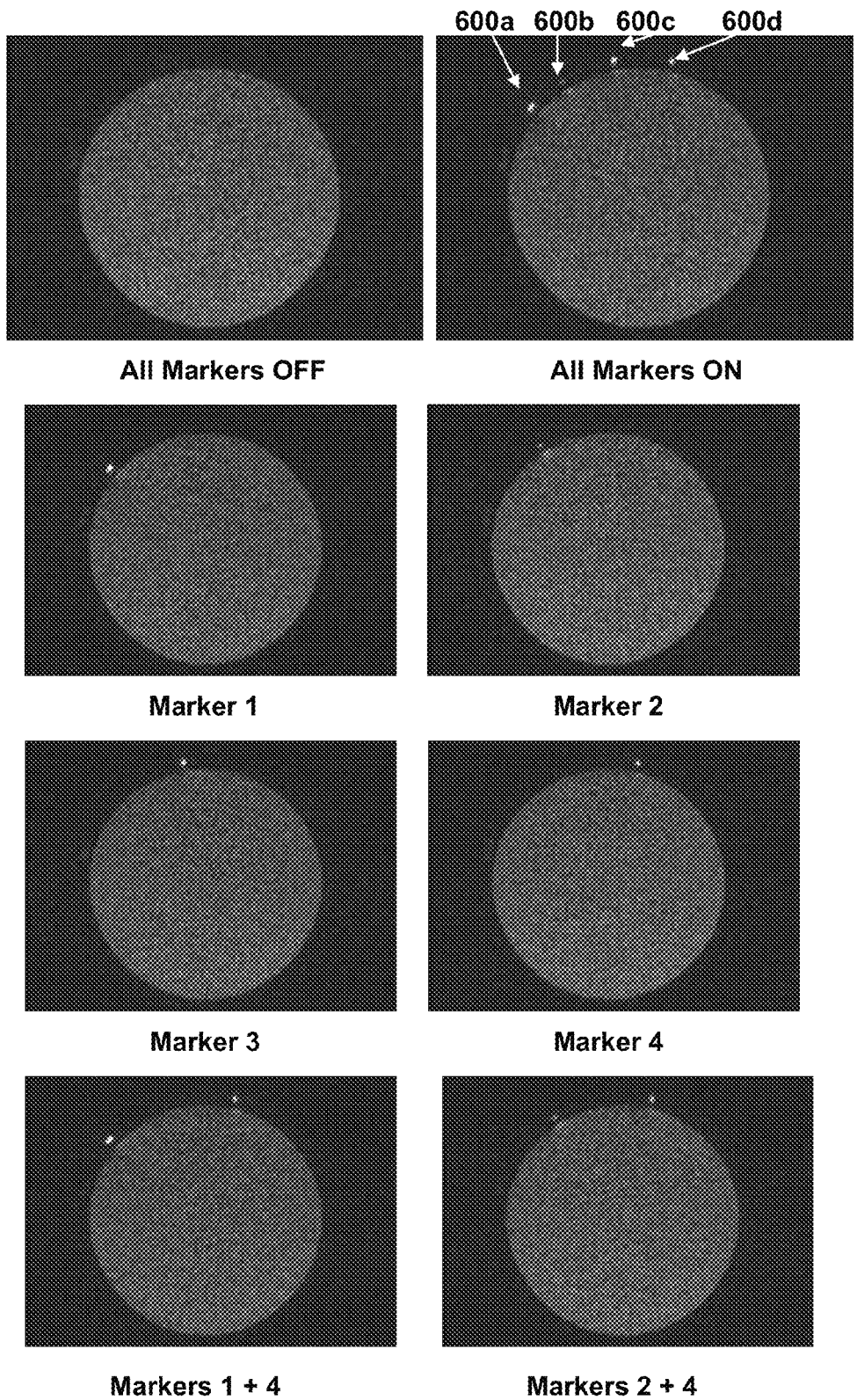
Figure 5L:
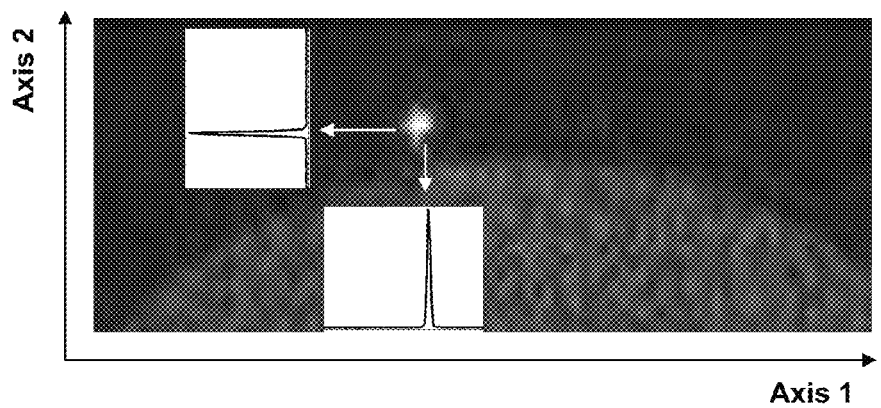

FIG. 5K shows results for a 4 marker set up that shows the selective detuning of ALL coils 610, tuning of ALL coils 620, sequentially tuning coils 1 630, 1 635, 2 640, 3 645, 4 650, 1+4 655, 2+4 660. FIG. 5L shows a zoomed in perspective of marker 3 illustrating the extraction of coordinates of the marker in the MR scanner coordinate system relative to the two axis defined by the imaging plane, entailing the generation of SI projections and identification of the signal peak that corresponds to the coil. In those case that a low flip angle was used for imaging, the signal for the background may be further eliminated by thresholding.

Generally, when more than one marker is used, it is not straightforward to identify which peak corresponds to which marker. Thus, the scheme depicted in FIG. 5B is used to make the markers MR-distinguishable and to avoid a high number of acquisitions and post-processing. This selectively turns a marker on, by tuning it, when it is tracked, and turns it off, by detuning it, when another marker is tracked. The method utilizes photodiodes and optical fibers controlled by the Data Scheduling module of the computational core. It is noted that inductively coupled coils operate with low excitation pulses, e.g., 1-2° in FIG. 5A, so that the surrounding tissue is minimally excited, if measurable at all, eliminating any unwanted background signal.

In another aspect there are provided methods for detecting the robot. While the fiducial marker method, as described herein, can provide a fast reconstruction $R_{FM}(t)$ of the robot, to detect the entire robotic device in 3D, an MR pulse sequence, herein referred as multiple projection imaging (MPI) is used. The approach collects thick slab 2D projections, $PR_{XY}(t)$, $PR_{YZ}(t)$ and $PR_{ZX}(t)$ onto the principal planes of the scanner coordinate system, as schematically depicted in FIG. 3A, whereupon the object can be reconstructed with back-projection.

Figure 6A:
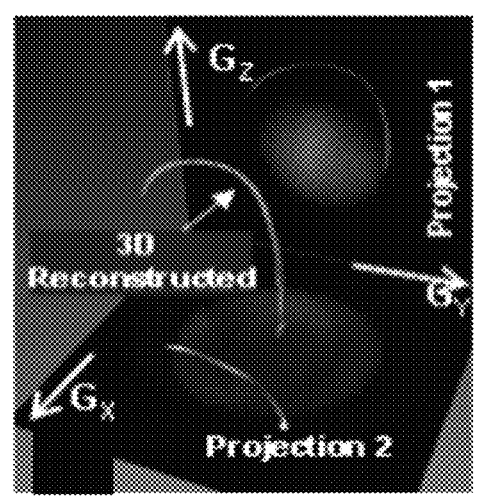
FIGS. 6A-6B illustrate a catheter MPI with speeds of 170 ms (FIG. 6A) and 49 ms (FIG. 6B) per 2D-projection.
Figure 6B:
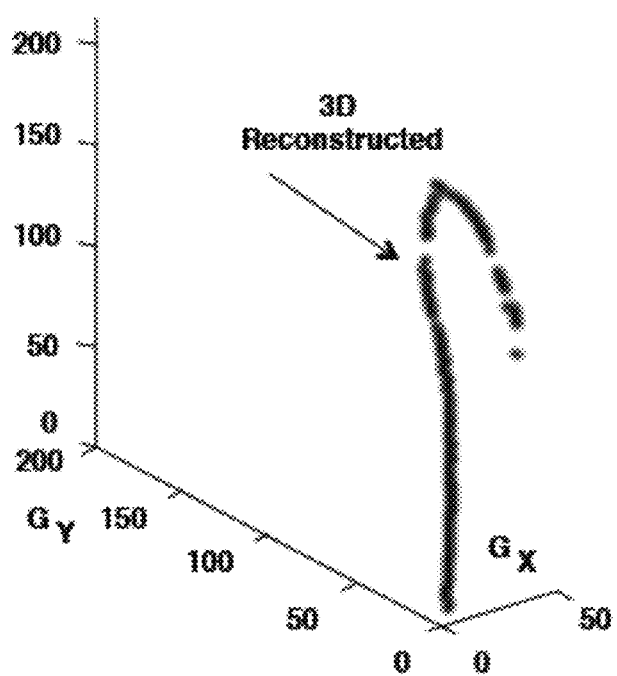

FIG. 6A shows the results of imaging a tube, filled with a Gd-contrast agent, attached to a spherical phantom. The T1-weighted MPI collected two projections $PR_{XY}(t)$ and $PR_{ZY}(t)$ at a speed of 170 ms. Using a novel reconstruction algorithm, the tube was accurately reconstructed in 3D with excellent matching with that generated from standard multislice MRI. FIG. 6B shows a similar reconstruction collected with higher speeds of 49 ms/projection. In both cases only two orthogonal projections were collected, however, a third can also be added to improve reconstruction. It is then straightforward to generate the virtual robot $R_{PR}(t)$ from the MPI reconstructed object.

Ideal operation of MRI is achieved when only the robot is visible in the MR images. This requires eliminating the background tissue signal by, for example, filling a channel in the robot with a gadolinium contrast agent and/or surrounding the channel with coil(s), such as in FIG. 4A. It also must be determined how many MPI projections (and how frequently are they collected) are sufficient for accurate reconstruction of the robot. Since the fiducial markers provide a first approximation of the robot, then it may be sufficient to collect only one or two 2D projections. Furthermore, the effect of the fiducial marker and MPI scheduling on the accuracy of the $R_{FM}(t)$ and $R_{PR}(t)$ as well as on the composite $R(t)$ generated by combining both of them should be determined.

In yet another aspect of this preferred embodiment there are provided methods for end-effector mounted loco-regional bio-sensing. This enables the operator to locally interrogate the tissue during the procedure. The operator can characterize tissue. e.g., differentiate malignant vs. benign, and/or to better define tumor margins. Also, the operator can assess tissue behind its surface, i.e., the boundary accessible with visual light endoscopy. In addition, the operator can spatially co-register loco-regional data to the robot coordinate system, i.e., to that of the MR scanner.

Figures 7A, 7B, 7C:
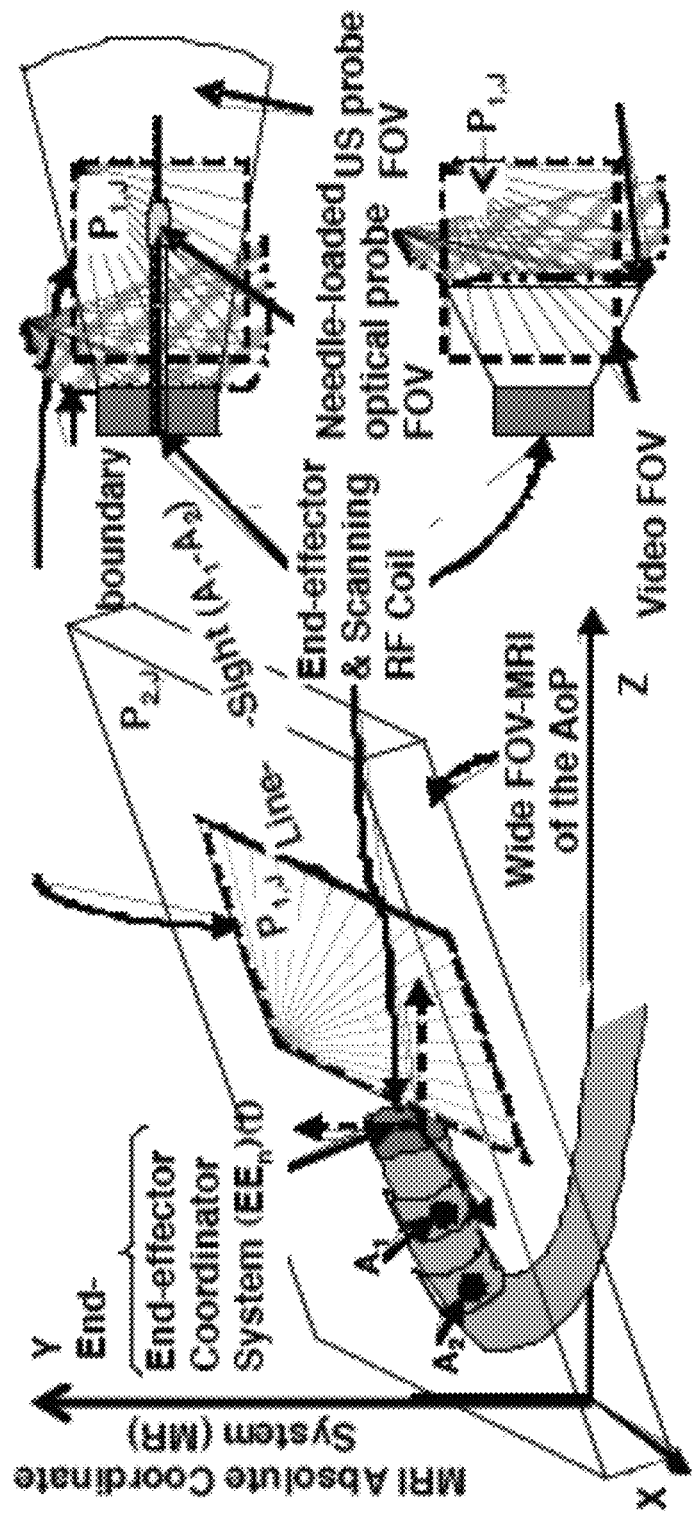
FIGS. 7A-7E illustrate loco-regional bio-sensing depicting a review of loco-regional bio-sensing (FIG. 7A), spatial scanning of a dual MR (FIG. 7B) and optical (LIF) sensor (FIG. 7C) with an MR-compatible robot of a three compartment phantom and the collection of inherently co-registered MRS (FIG. 7D) and LIF (FIG. 7E) data.
Figure 7D:
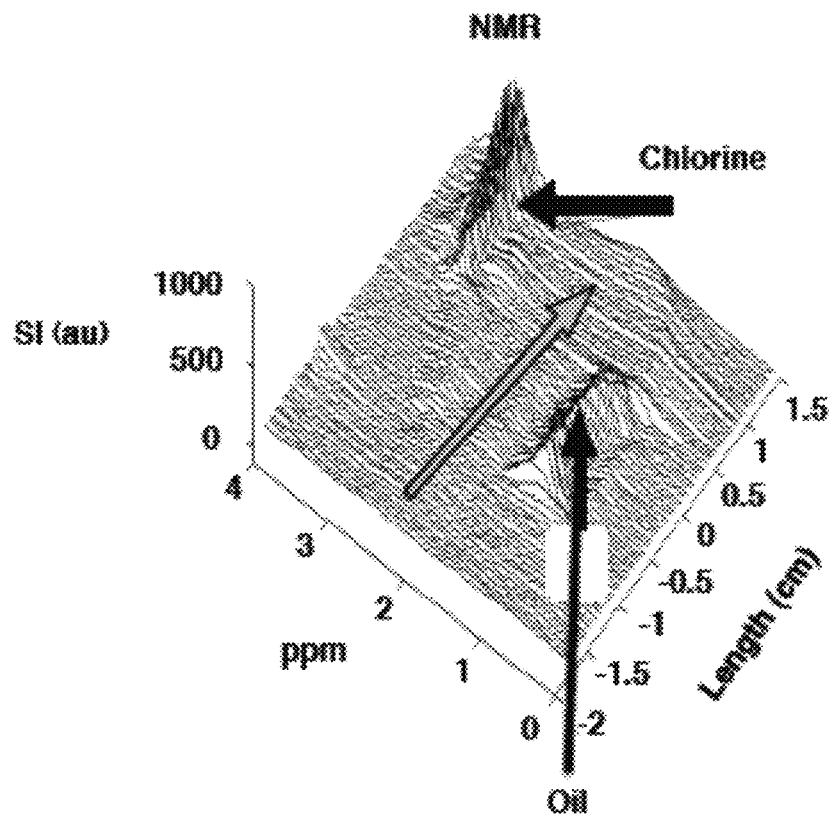
Figure 7E:
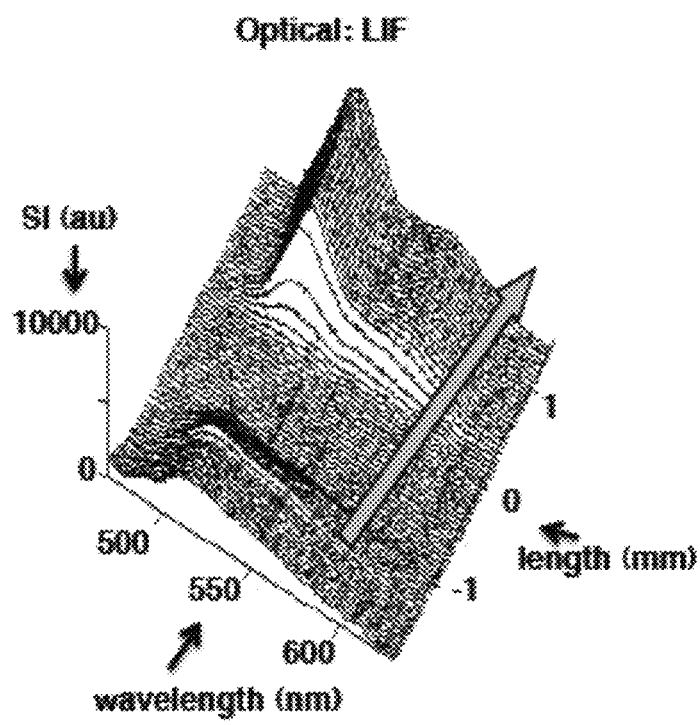

For example, as shown in FIG. 7A, the end effector carries an RF coil for localized high-sensitivity MR spectroscopy or high-resolution MRI, carries an optical sensor for light induced fluorescence (LIF) and carries an US sensor. FIGS. 7B-7C depict a prototype MR-compatible robotic scanner that carries a trans-needle probe with a miniature 1.1 mm Tx/Rx RF coil for collection of loco-regional MRS and registration, and an endoscopic LIF sensor with two 300 micron optical fibers for emission and one 300 micron optical fiber for reception. Using microprocessor-based control that manages the automated interleaved collection of LIF and MRS, scanning was performed with this robot. As shown in FIGS. 7D and 7E, the optical and MRS data matched the spatial distribution of chemicals and metabolites in three compartment phantoms.

Figure 8:
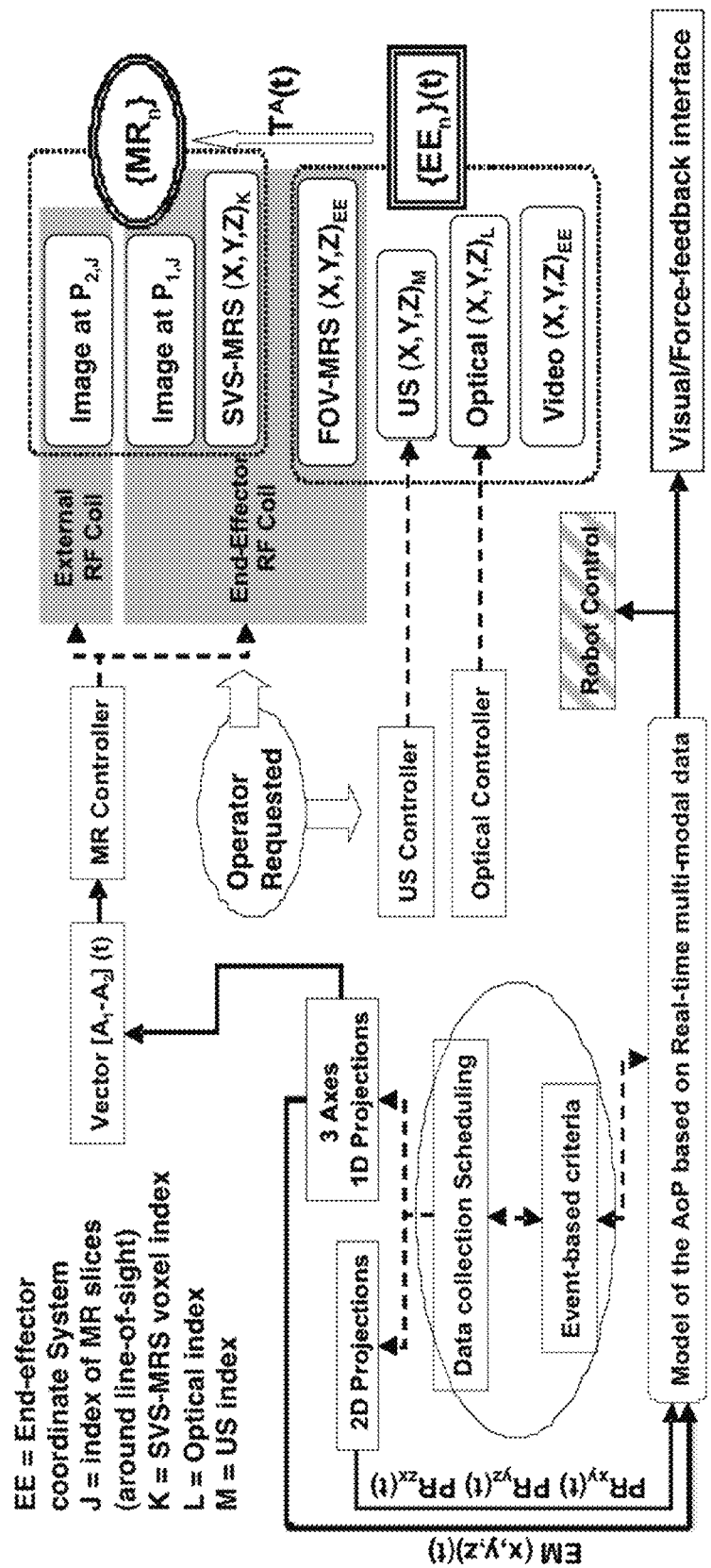
FIG. 8 illustrates the Interconnection of sensing with robot & scanner control.

It is contemplated that these bio-sensing methods require an RF coil, e.g., Rx or Tx/Rx, in which its sensitive area provides for scanning of the end-effector. The pulse sequences may require modification by outer volume suppression to reduce the sensitive area of detection. Also required, is a mechanical assembly for advancing the LIF probe during scanning and an ultrasound probe, such as configured for A-line or M-mode imaging, and means to rotate the probe±90° thereby allowing selection of the orientation of the imaged sector. In addition, algorithms for fusing the co-registered data and presenting them to the operator via the HIMI are required. FIG. 8 illustrates the interconnections between biosensing with a robot and scanner control. Robot control and on-the-fly control of the MR scanner can be incorporated into the scheme at the point indicated.

In yet another aspect there is provided methods for linking control, the imaging scanners and the operator. Algorithms enable the interleaved acquisition of fiducial marker tracking and MPI, so that one complements the other in the generation of the R(t). Because state-of-the-art MR scanners provide their external control on-the-fly and provide for selection of imaging planes or contrast mechanisms, a software module is required that is configured to select, on-the-fly, which particular pulse sequence is to be used. This is intelligent adaptive control which enables the accurate generation of a dynamic 3D object, e.g., the robot, from a limited number of real-samples.

The algorithm also is configured for the multi-modal data co-registration to the MR scanner. Since loco-regional sensors are at known positions on the end-effector's coordinate system $\{EE_n\}$ and the end-effector position is tracked with the two most distal RF markers, $A_1$ and $A_2$ (FIGS. 3A and 7A), then the position of the source/detectors of the loco-regional sensors can be registered to the MR coordinate system $\{MR_n\}$ via the transformation matrix $T^4(t)$. The end-effector coordinate system and the matrix $T^4(t)$ change in time as the robot moves.

In yet another embodiment there is provided an image-based virtual model of the area of-procedure (AoP). Alternatively, visualization of the area of procedure and/or the robot may be implemented as a visual image, a virtual reality scene, an enhanced reality scene, etc. or any superimposition or combination thereof. As provided herein an on-the-fly model of the AoP for robot control and the HIMI, i.e., the visual/FFI, are updated continuously. This model is based on the real-time MR data and fuses the robot R(t) and the surrounding environment in the form of dynamic guidance conduits, which are virtual 4D passages from the entrance point to the target, within which the robot can maneuver safely without colliding with and harming vital structures or healthy tissue. Different spatio-temporal aspects of the model of the AoP are continuously updated as pertinent MR data is collected and is processed with a multi-thread multi-core processing architecture to achieve high rates of on-the-fly update. For example, FIGS. 9A-9B illustrate results from generating guidance conduits from real-time MRI images at 49 ms/image for intracardiac procedures via a trans-apical access for transversing the left ventricle (LV) for valvulopasties and for cardiac procedures via epicardial access in which a simulated virtual snake-like robot is included.

As described, the robot is detected and tracked from a limited number of fiducial markers, supplemented by fast but less-frequent 3D imaging of its entire length. Similarly, MR can be used to track the motion of the surrounding tissue from a limited number of points or boundary points, from MR images, based on the collaborative trackers algorithm, and from MR 1D projections. The "boundary points", are used to generate the dynamic guidance conduits, which is utilized both as input constrain to the control of the robot and to the man-in-the-loop control via the FFI, i.e., offering "expert" advice to the operator.

In one aspect of this preferred embodiment there is provided methods for tracking motion of surrounding tissue from boundary points utilizing a collaborative trackers algorithm. Boundary points are extracted from fast anatomical images with their orientation automatically updated on-the-fly to include the robot and surrounding tissue of interest by tracking specific landmarks. Based on a Bayesian network of collaborative particle filter-trackers, this algorithm can track landmarks even when encountering sudden motions or significant changes in morphology. For example, the algorithm can track the apex, midline of LV, and the base of aortic valve annulus with a processing speed of 25-40 fps on a standard computer. Particularly for landmark tracking, the collaborative trackers method, based on particle filtering, is an optimized tracking mechanism, free of strong modeling, which can accommodate very efficiently a predict-update loop. To address instabilities of a single particle filter tracker to sudden motion or large appearance changes, that occur in a surgical procedure, especially in the heart or the abdomen, processes comprising a collaborative tracking framework that coordinates multiple particle filter trackers and a Bayesian network method to decide which trackers fail and which ones survive at each time step were used. The algorithm is integrated into the multi-thread computational core. The collaborative trackers method and algorithm can be utilized for tracking landmarks selected by the surgeon on real-time images pertinent to the different surgical models and can accommodate 3D tracking of an area from sets of oblique-to-each-other MR slices.

Figure 10B:
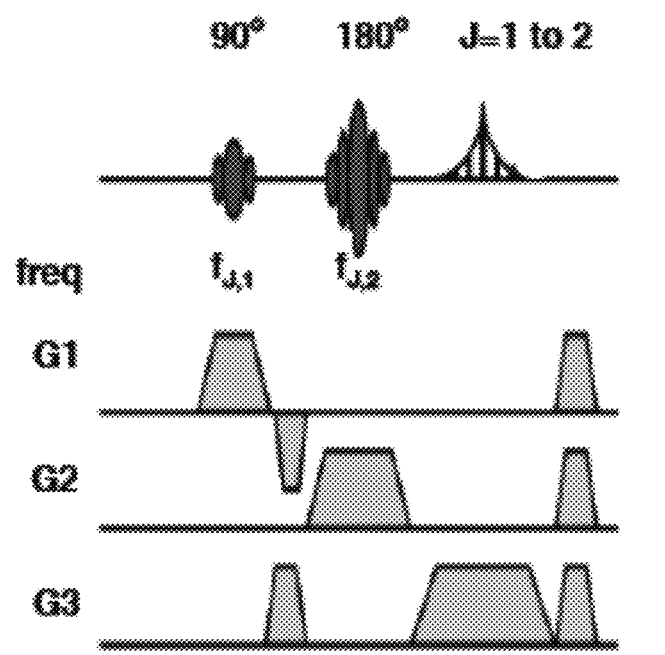

In another aspect there is provided methods for tracking motion of surrounding tissue from boundary points utilizing magnetic resonance projections instead of MR images. MR allows selecting and acquiring the signal, such as a 1D SI signal, from columns set, for example, but not limited to, obliquely or orthogonally, to the transient position of the robot, as is done in navigator echo, illustrated in FIG. 10A. In the method columns of virtually any position, size and orientation can be selected. Using a selected MR pulse sequence, such as is shown in FIG. 10B, the 90° pulse selects a plane while the 180° pulse focuses only spins that belong to the column. In the presence of the read-out gradient a projection is then generated along the axis of the column achieving speeds of 4-5 ms ms/projection.

In utilizing these methods, the effect of column width on the signal-to-noise ratio (SNR) and accuracy of extracting the boundary points must be considered because wider bands increase the SNR but decrease resolution since more tissue is averaged. Also, the number and position of columns/projections on the accuracy of the dynamic model of the tissue must be considered. The methods also require SI processing algorithms for identifying landmarks of interest and calculating their transient position.

Figure 10C:
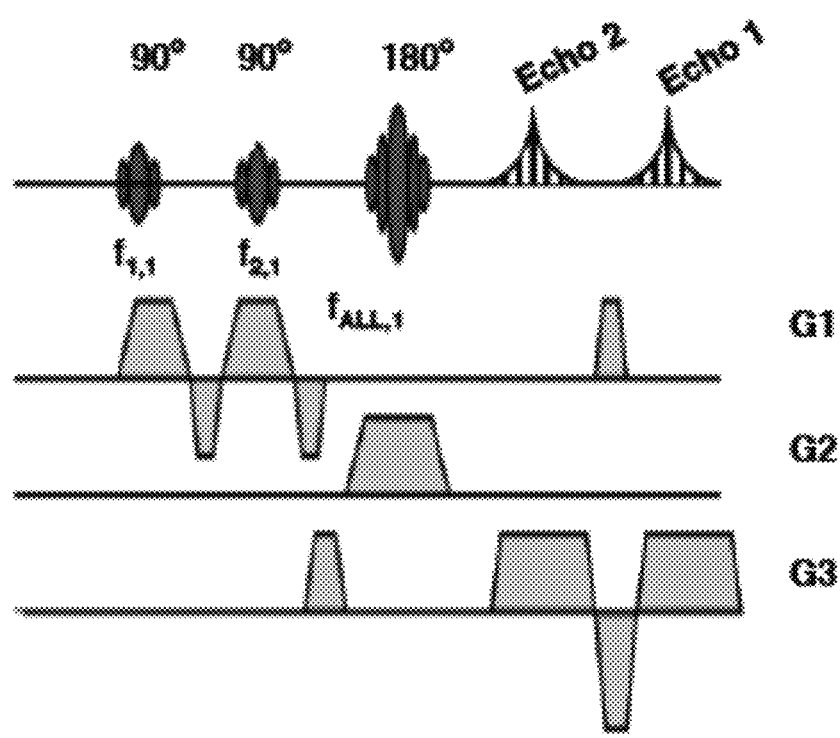

Alternatively, a pulse sequence, such as illustrated in FIG. 10C, can be used to collect projections from all the columns that share a common slice at the same repetition of the sequence, i.e. in one repetition time TR, thus even further speed up data acquisition. The series of N 90° pulses excites N oblique planes, the common 180° pulse refocuses all the columns generating N echoes. The reverse order of echoes and the requirement for balancing the gradients along all axes is necessary to achieve the series of echoes from the different columns. These methods, while far faster than collecting images for the collaborative trackers, can only be used if the projections exhibit SI features clearly related to the landmarks of interest. In a non-limiting example, the method is applicable to imaging the heart.

In yet another aspect there is provided methods for generating dynamic guidance conduits from a limited number of boundary points. Generating the 4D guidance conduits enables covering a wide area of tissue along the entire path of the robot with maximum possible refreshing rates. To achieve this, parallel algorithms will be utilized, expanding upon our aforementioned preliminary work. After an initial manual prescription of the areas of tissue used to monitor their motions, parallel algorithms can perform the following in real-time:

1. Extract the boundary points. The term "limited" is used to denote that only a small number of traceable points are practically available at any instance. These points are generated on-the-fly from one or both methods utilizing boundary points from collaborative trackers or MR projections, as described herein.

2. Generation of dynamic control curves by fitting splines on the boundary points so that the number of interpolated points remains the same on each curve. As the boundary points are dynamic, adhering to the natural motion of tissue, or its displacement, the dynamic control curves inherit this property.

3. Generation of dynamic guidance conduits (FIGS. 10A-10B) by connecting the interpolated points from the boundary to form a coarse mesh, which is further processed to form a refined mesh that is the allowable space for safe automated or manual maneuvering of the robot to the target.

4. Update of the robot model calculated on-the-fly from MR tracking, as described herein, and fusion with the dynamic guidance conduits, as depicted in FIG. 8.

In yet another embodiment there is provided methods for generating virtual entities for robot control and HIMI. The method generates dynamic access corridors, which is a computer-generated 4D tubular structure from the site of entrance or apex to the targeted anatomy, e.g., the aorta, within which the interventional tool can maneuver safely without collision and harm to vital structures or healthy tissue. The method also generates dynamic guidance trajectories along which the tool should be aligned to safely and accurately reach the target.

For example, in a transcatheter aortic valve implant (TAVI) paradigm, generation of dynamic models requires that the robot does not harm structures in the LV, e.g. endocardium, mitral leaflets or papillary muscles, and that the robot guides the end-effector from the apical entrance to the targeted center of the aortic annulus. These dynamic models are used to constrain both the control of the robot for safety and accuracy and the man-in-the-loop control via force-feedback interfacing, i.e. offer "expert" advice to the operator.

Figures 11A, 11B:
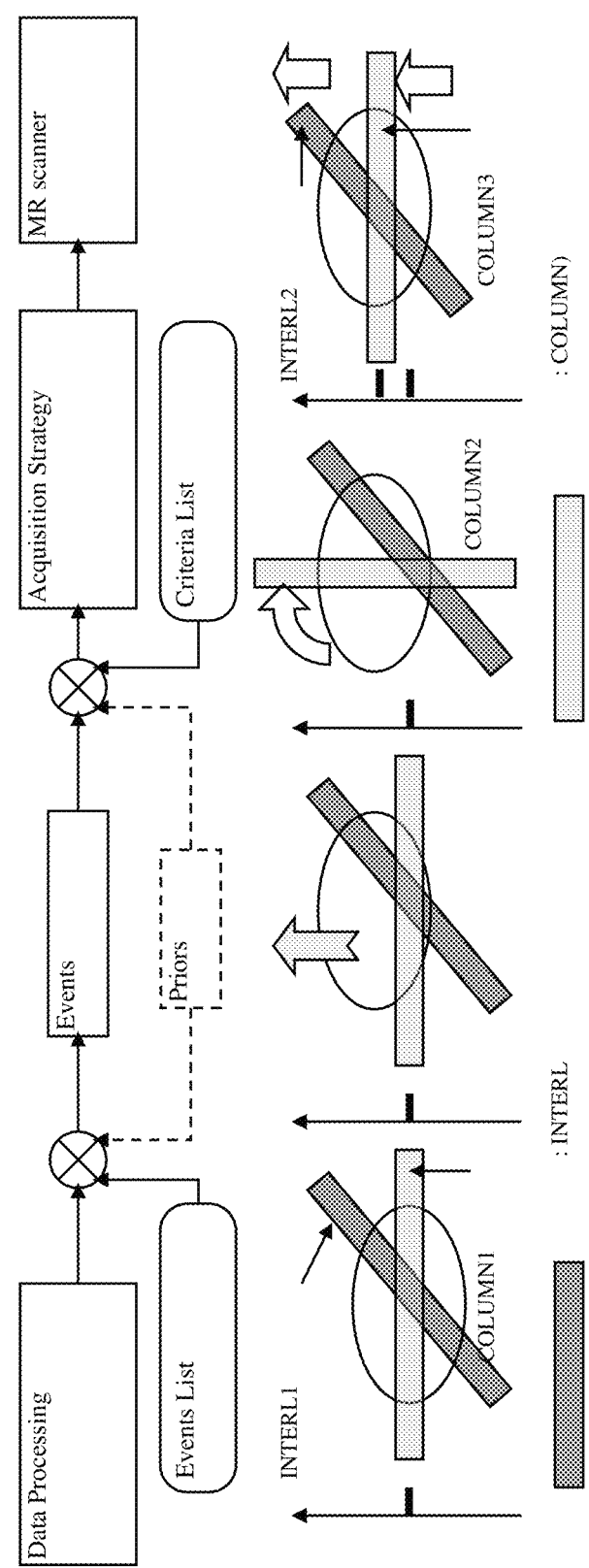
FIGS. 11A-11B depict the software module MR scanner control (FIG. 11A) and an example of its operation (FIG. 11B).

According to another preferred embodiment, is a software module for the control of the MR scanner on-the-fly to improved sensing during the procedure. It uses the capability of current clinical MR scanners for changing the acquisition parameters on-the-fly, as an example has shown before in MR-guided vascular interventions [8] and by Christoforou et al that described the first-ever integration of robot and MR scanner for spatio-temporal matching of robot and imaging plane for enhanced and intuitive human-in-the-loop control [9]. The operation of this module is an event-triggered response: events occurring during the procedure determine the type of MR data that will be subsequently collected. FIG. 11A shows a suggested module with three processes.

1. Process data, pertinent to the tissue, such as an image-generated dynamic model area of the procedure AoP(t)), and the robot, such as the kinematic status of the robot Robot-State(t)), to calculate measures of changes, such as sustained reduction in the width of the access corridor, or the size of a targeted lesion.

2. Identify triggering events by comparing the above changes to a list of criteria in the form of range-of-values using simple conditional algorithmic approaches or using artificial intelligence/machine learning algorithms.

3. Select a response from a database and determine a new acquisition strategy, i.e. type and frequency of MR data to be collected MRAcq(t)), and send it to the MR scanner as example but not limited to via a dedicated TCP/IP.

FIG. 11B illustrates an example of the operation of the module for a hypothetical case where the targeted lesion (oval shape) moves out-of-plane due to the advancement of the tool. In this example, it is assumed that the lesion does not change size due to natural phenomena, e.g. the LV of the beating heart. This will cause a reduction of its width on the signal profile of a projection column (COLUMN1) relative to its prior size, sustained over several repetitions. Such change will trigger the module to order a COLUMN2 orthogonal to the prior one. When the module identifies from the profile of COLUMN2 that the lesion is repositioned, it commands a new MRAcq(t) updating the center of both COLUMN3 and the slices(s) of interleaved slices (INTERL2) to match the new position of the lesion. Some of such cases of events and responses are: (i) if a sustained decrease of the access corridor is observed during heart systole, the response must be to increase COLUMN collection frequency in this area, (ii) as the distal tip of the tool reaches the target, then collect radial pattern INTERL (around the target-to-tool axis) and increase frequency of MARK, and (iii) if SNR is reduced then widen the width of the COLUMN. A comprehensive list of events can be compiled including criteria and responses. Furthermore, event calibration is incorporated, i.e. what extent of the event causes what response. The events can also be classified in an order of significance to improve the module's algorithm.

Figures 12A, 12B:
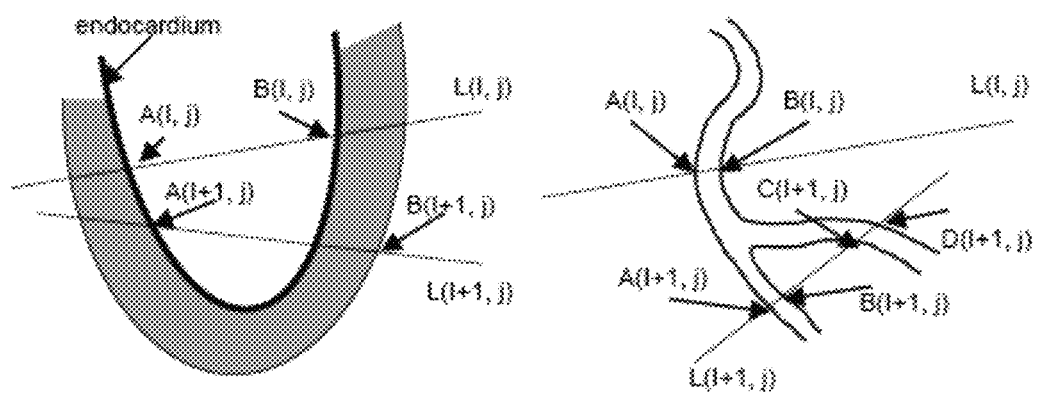
FIGS. 12A-12D depict dynamic tracking of tissue with multiple projections for monitoring tissue boundaries of the LV endocardium (FIG. 12A) and a vessel (FIG. 12B) and, optionally, using contrast agents (FIG. 12C) or a magnetization preparation to simplify the form of the projection signal (FIG. 12D).
Figures 12C, 12D:
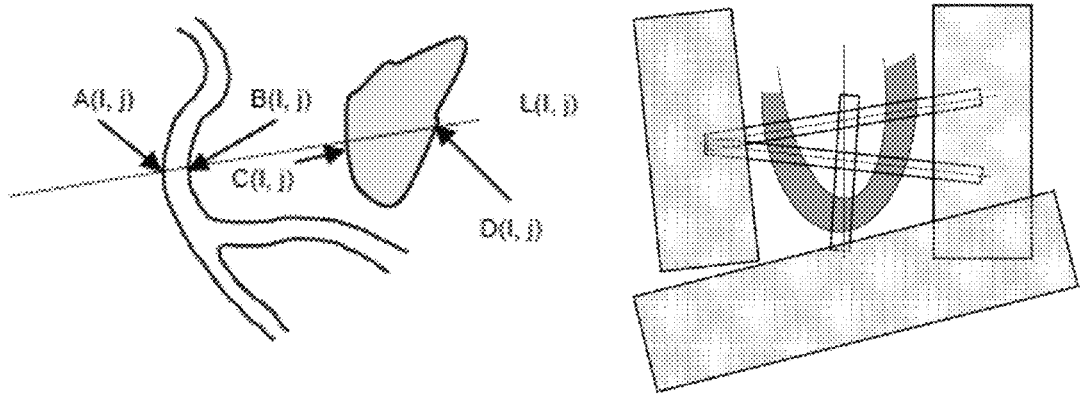

In yet another preferred embodiment there is provided dynamic tracking of tissue with multiple projections that are strategically placed to monitor the motion of specific tissue boundaries. For example, FIGS. 12A and 12B illustrate dynamic tracking for the LV endocardium and a vessel, respectively. In one aspect, as shown in FIG. 12C, the imaging sequences are selected and parameters are set to generate contrast differences. This contrast can be generated by the infusion of exogenous contrast agents. The points AJ, BJ, CJ, and DJ are extracted from the projections, which are denoted with Lines LJ and LJ+1, that are then combined to generate the tissue boundary of interest. In another aspect, as shown in FIG. 12D, a special magnetization preparation, such as "saturation band", can be applied to restrict the length of the collected projection to simplify the form of the projection signal.

Figure 13A:
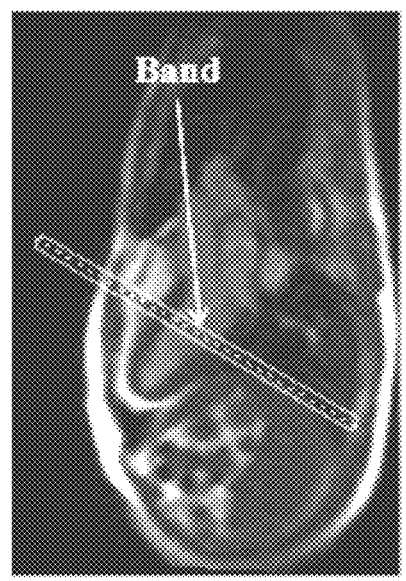
FIGS. 13A-13B depict accessing available SNR and contrast differences for projections.
Figure 13B:
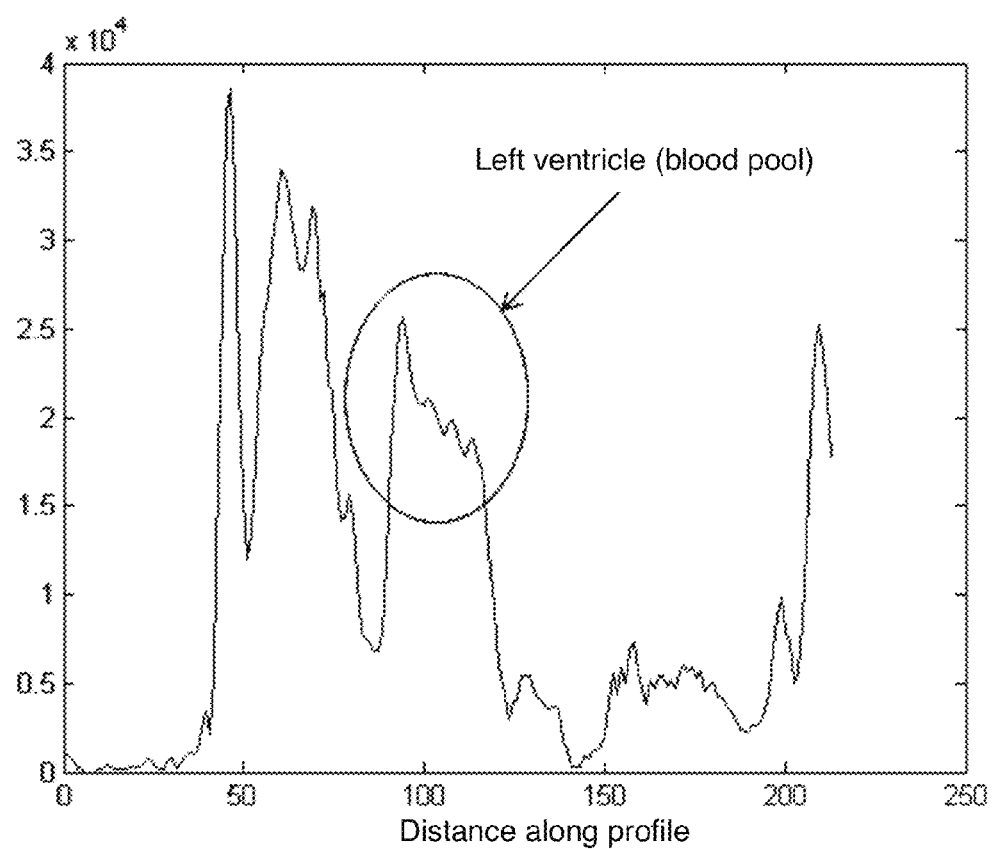

For example, FIGS. 13A and 13B illustrate a preliminary analysis to the available SNR and contrast differences for projections. Specifically, the original dynamic MR image shows the projection line and the width of the area that the signal integrated. The graph of the signal illustrates the LV and the two deeps left/right that correspond to myocardium.

Figure 14:
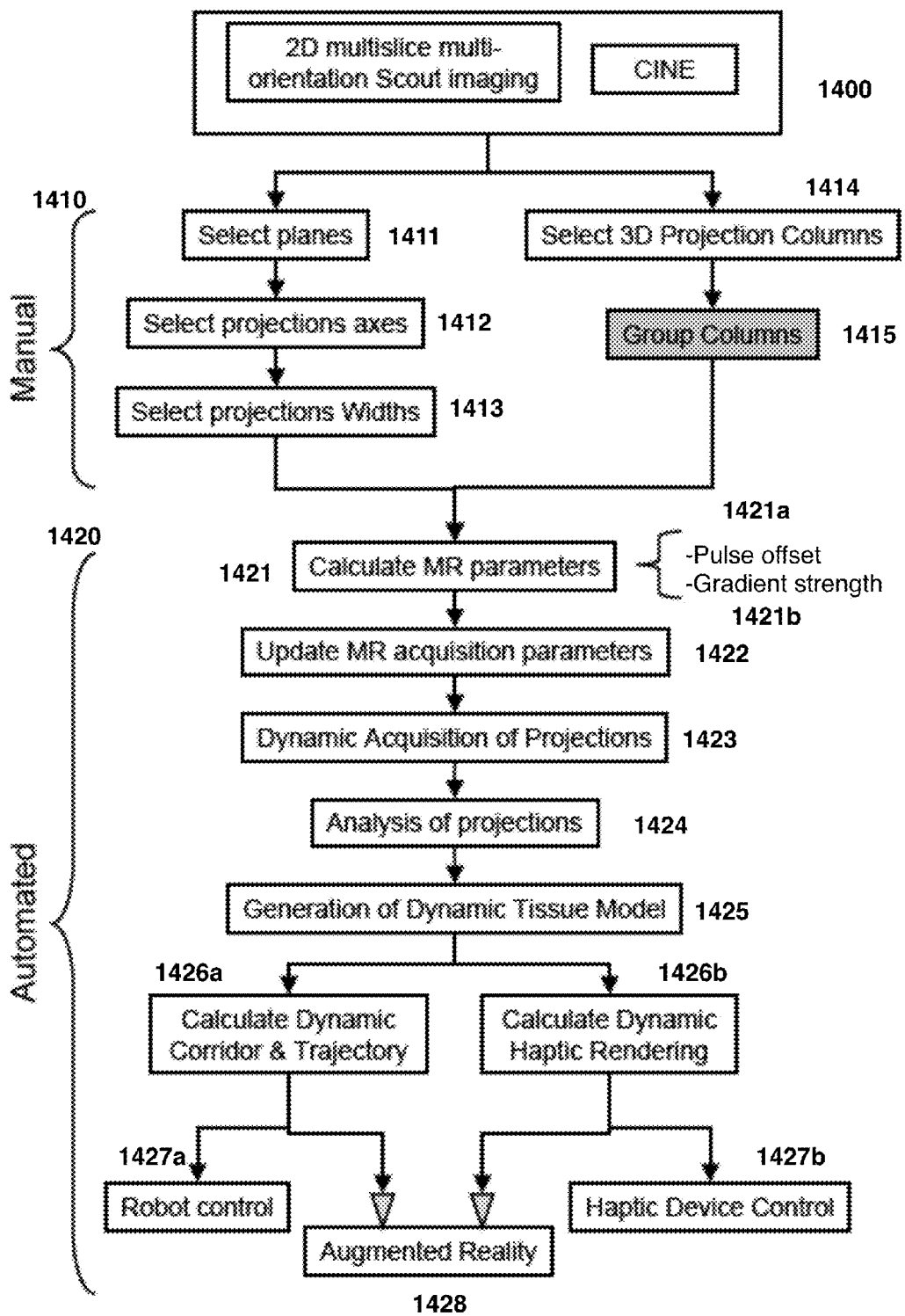
FIG. 14 is a flowchart of the method for robotic surgery control.

The method for robotic surgery control is depicted in FIG. 14. For 2D multislice multi-orientation Scout imaging/CINE 1400, there are manual 1410 and automated 1420 components. First, manually, the planes 1411, projection axes 1412 and projection widths 1413 are selected concomitantly with selection of 3D projection columns 1414 which are then grouped at 1415. From this, using automation, the MR parameters are calculated 1421, i.e., the pulse gradient 1421a and the gradient strength 1421b. Then sequentially, the MR acquisition parameters are updated 1422, a dynamic acquisition of projections is performed 1423, the projections are analyzed 1424, and the dynamic tissue model Is generated 1425. After these steps the dynamic corridor and trajectory is calculated 1426a along with the dynamic haptic rendering 1426b that results in robot control 1427a and haptic device control 1427b, respectively, and, from both calculations 1427a,b, augmented reality 1428 is produced.

Figure 15A:
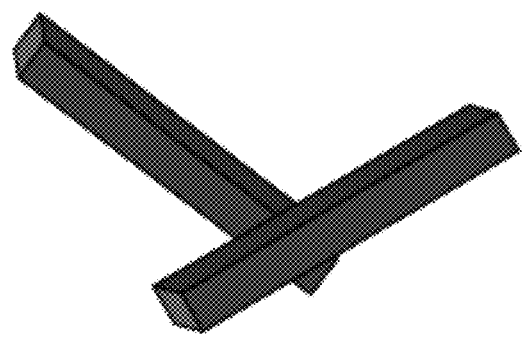
FIGS. 15A-15B depict the utilization of arbitrary columns and/or arbitrary orientations of projection columns to select projection columns that are not (FIG. 15A) and are (FIG. 15B) based on a common slab.
Figure 15B:
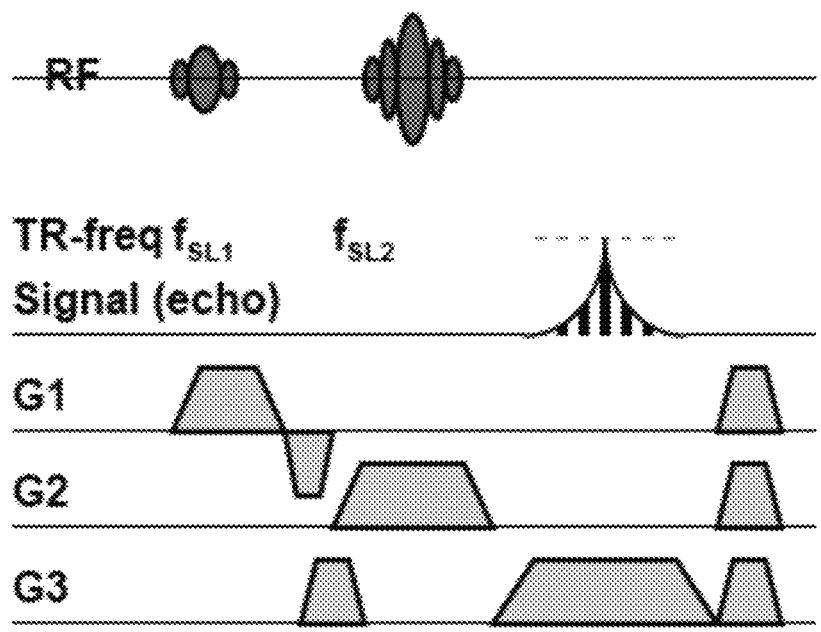

Also, in this preferred embodiment, FIGS. 15A and 15B, show how arbitrary columns and arbitrary orientations of projection columns can be utilized to select projection columns that are not and that are based on a common slab, respectively. For example, FIG. 15A illustrates an arbitrary selection of columns when there is not a common slab. When there is a common slab and arbitrary columns are utilized, FIG. 15B illustrates a pulse sequence based on the traditional Spin-echo can be modified by removing the encoding gradients and accordingly arrange the excitation and 180 refocusing pulse selection gradients and RF transmission frequencies that enables the selection of projection columns.

Figure 16A:
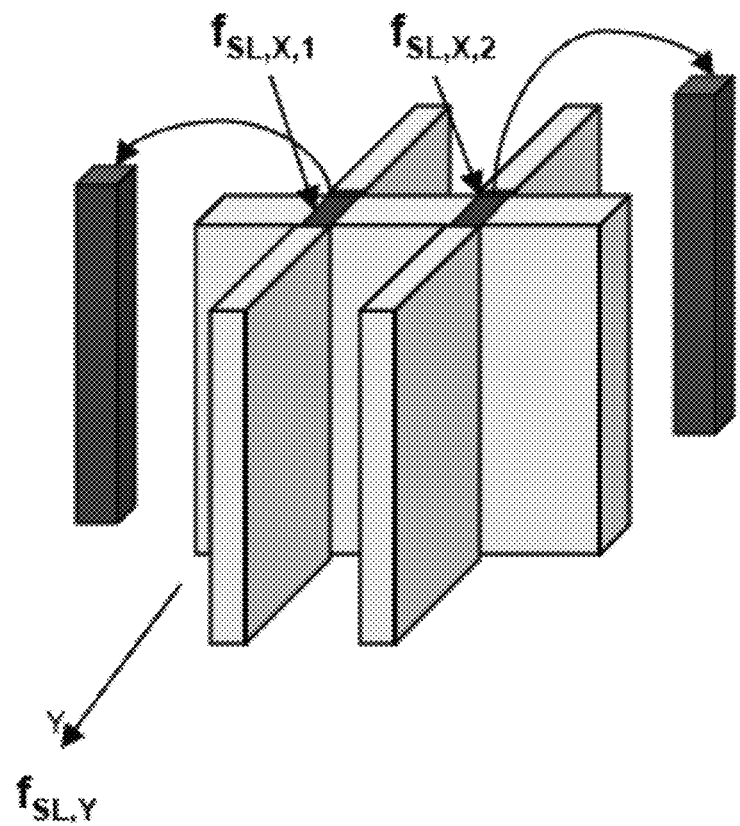
FIGS. 16A-16B depict the selection of two projection columns of a common slice on the Y-axis (FIG. 16A) and the selection of three projections with an arbitrary orientation to the main slice (FIG. 16B).
Figure 16B:
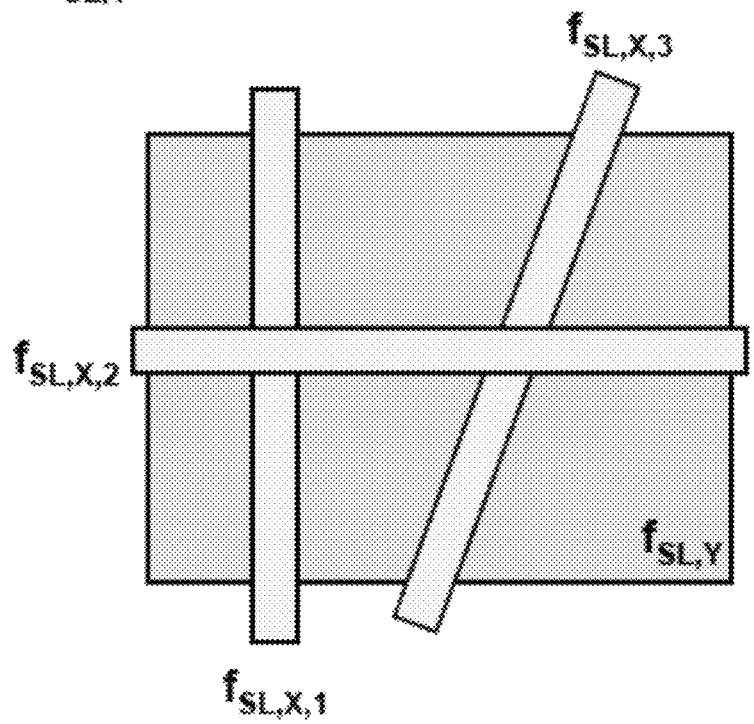

Particularly, FIG. 16A illustrates the selection of two projection columns that are composed of a common slice at axis Y. The frequencies correspond to the RF pulse transmission frequencies pertinent to the following pulse sequences. The two projection columns are the common space of the three slices/slabs. The selection of three projections that are of arbitrary orientation relative to the main slice is shown in FIG. 16B. Three projections are useful for monitoring tissue at different orientations.

Figure 17A:
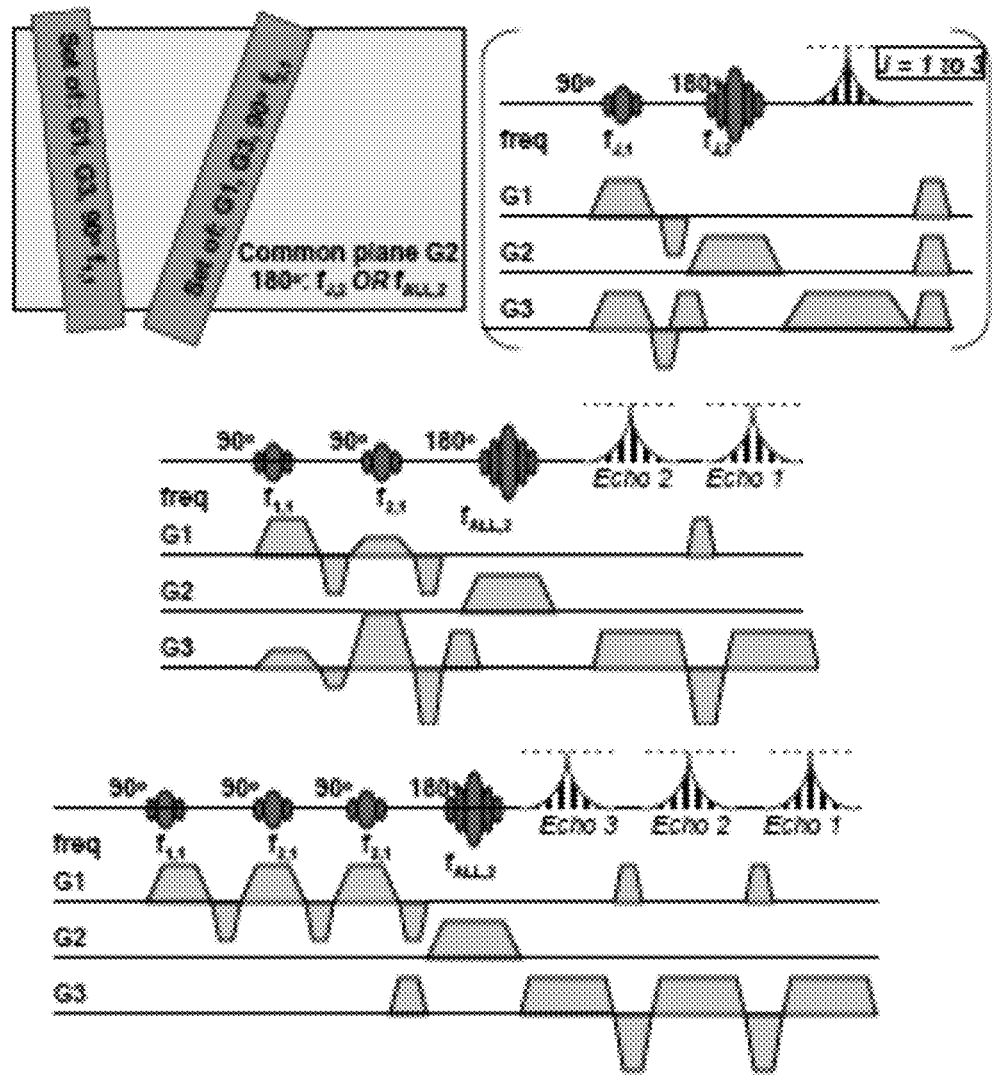
FIGS. 17A-17E depict type I multi-projection pulse sequences (FIG. 17A) and balancing the gradients thereof (FIGS. 17B-17E).
Figure 17B:
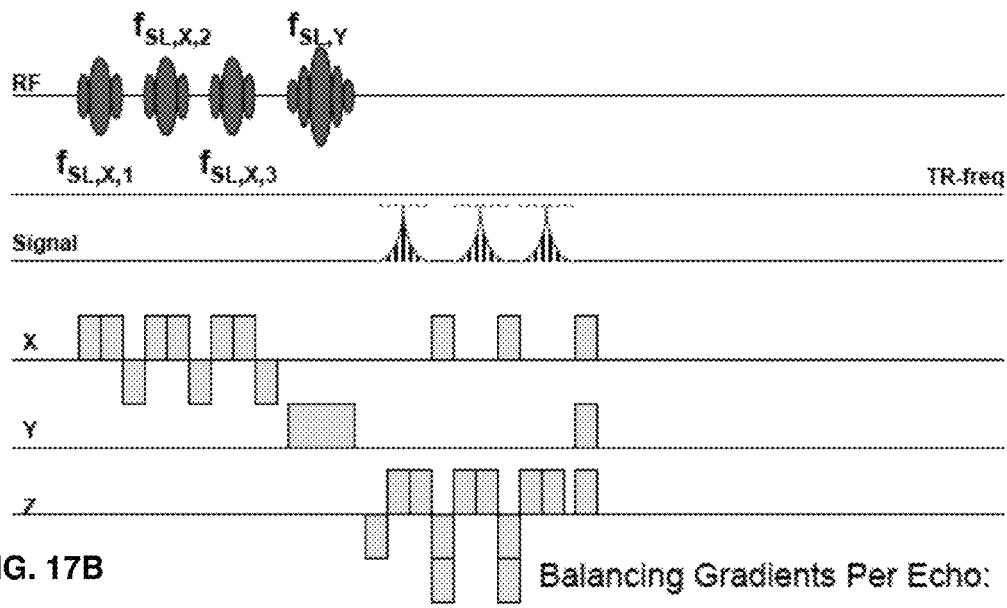
Figure 17C:
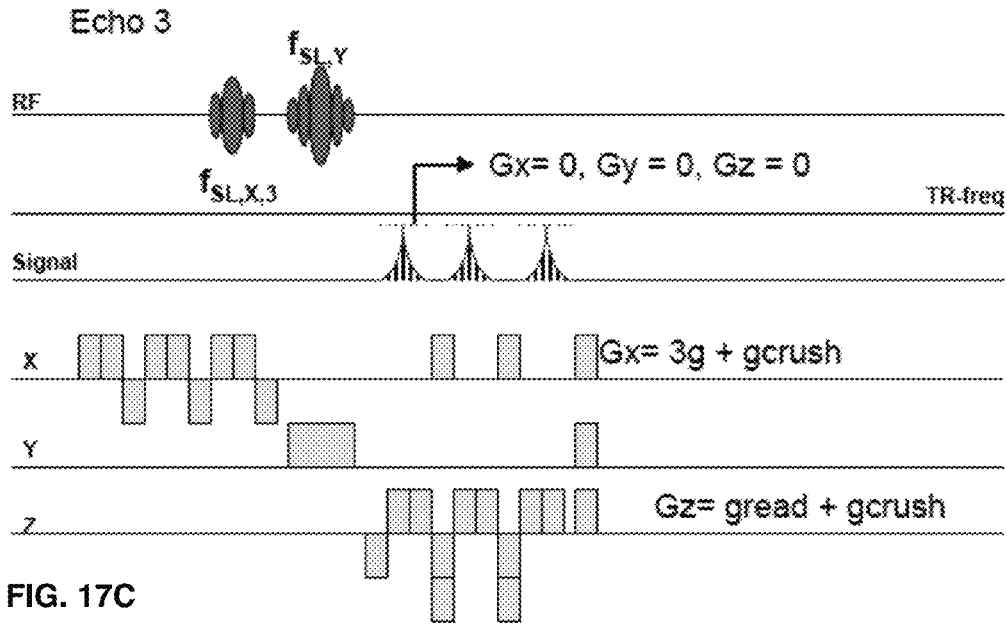
Figure 17D:
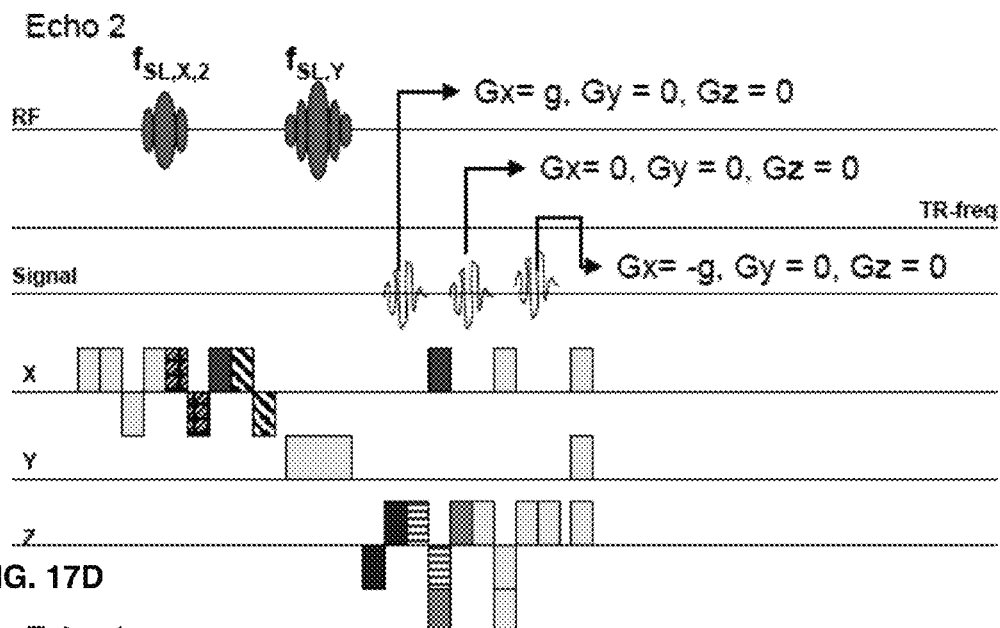
Figure 17E:
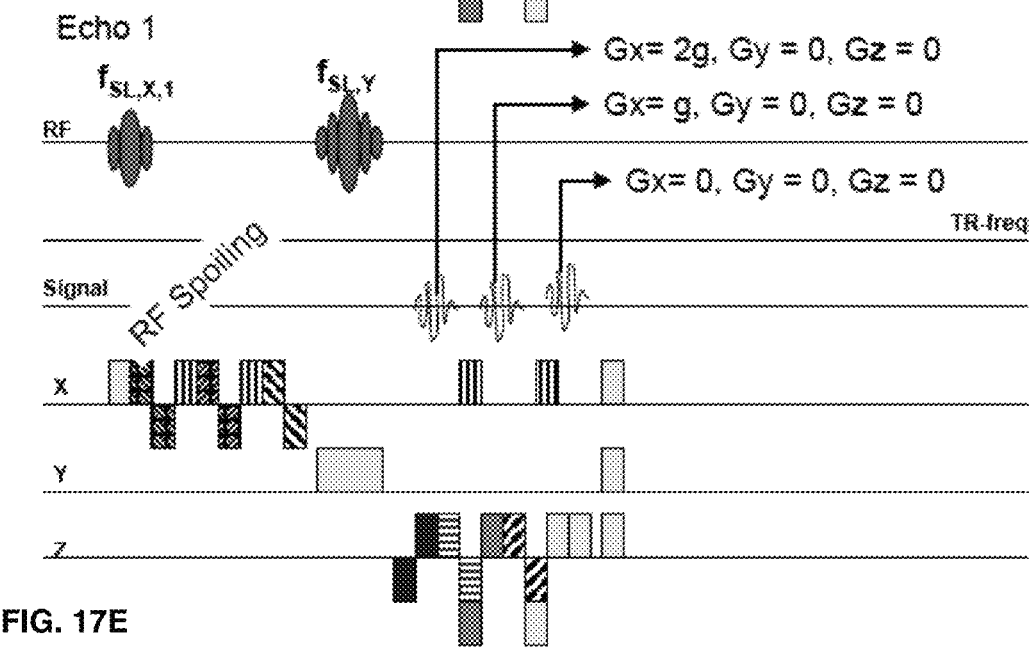

In this preferred embodiment, FIGS. 17A to 17E illustrate multi-projection pulse sequences of type I and gradient balancing thereof. As shown in FIG. 17A, this sequence has three units for the: 1) multi-slice selection with slice refocusing (X-axis), 2) inversion pulse refocusing with selection of the common slice (Y axis) and 3) multiple read-out train, like an EPI. Gradients are balanced along the X- and Z-axes to account for the application of gradients. FIGS. 17B-17E show, pictorially, balancing of the gradients for type I pulse sequences. The sequence can be extended to include multiple zones on the same common slice. It is important to note that each slice selection generates its own independent signal that is subject to a) any gradient applied after it, b) the inversion pulse and c) the read-out gradients.

Figure 18A:
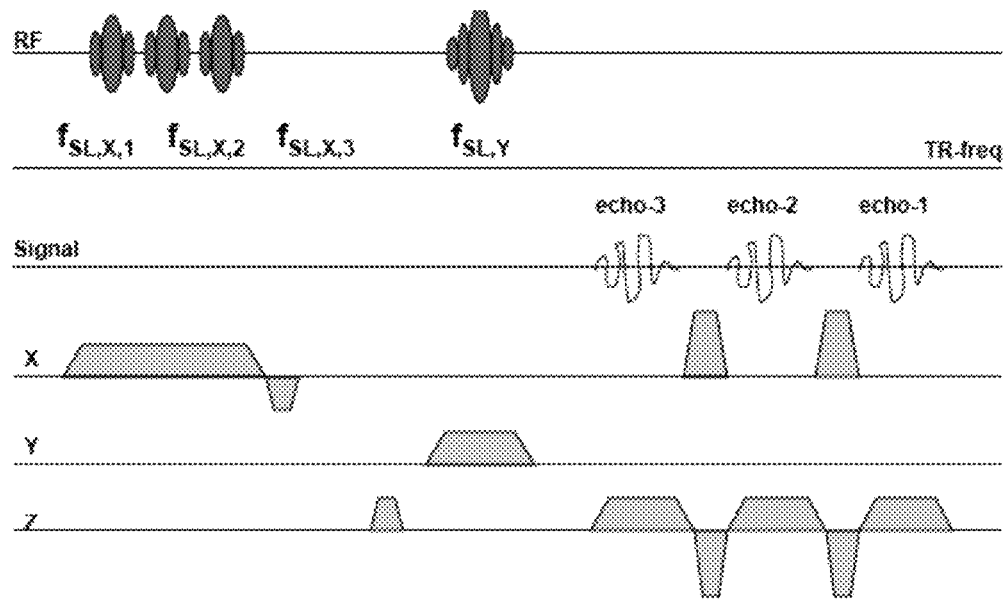
FIGS. 18A-18F depict type II multi-projection pulse sequences (FIG. 18A) and balancing the gradients thereof (FIGS. 18B-18E) and an alternative type II pulse sequence utilizing single slice selection (FIG. 18F).
Figure 18F:
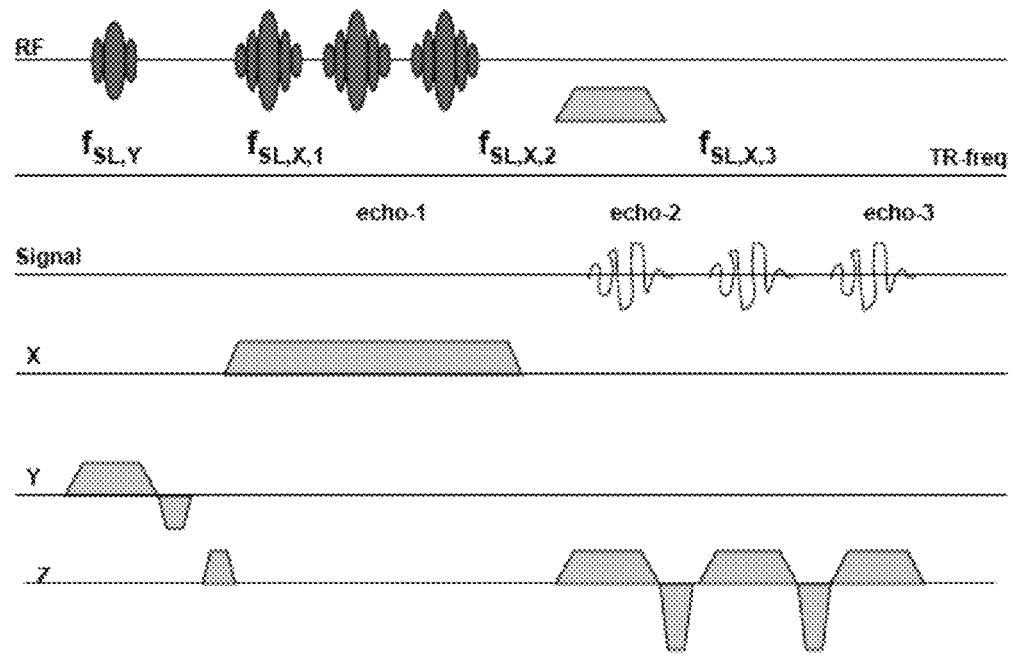
Figure 18B:
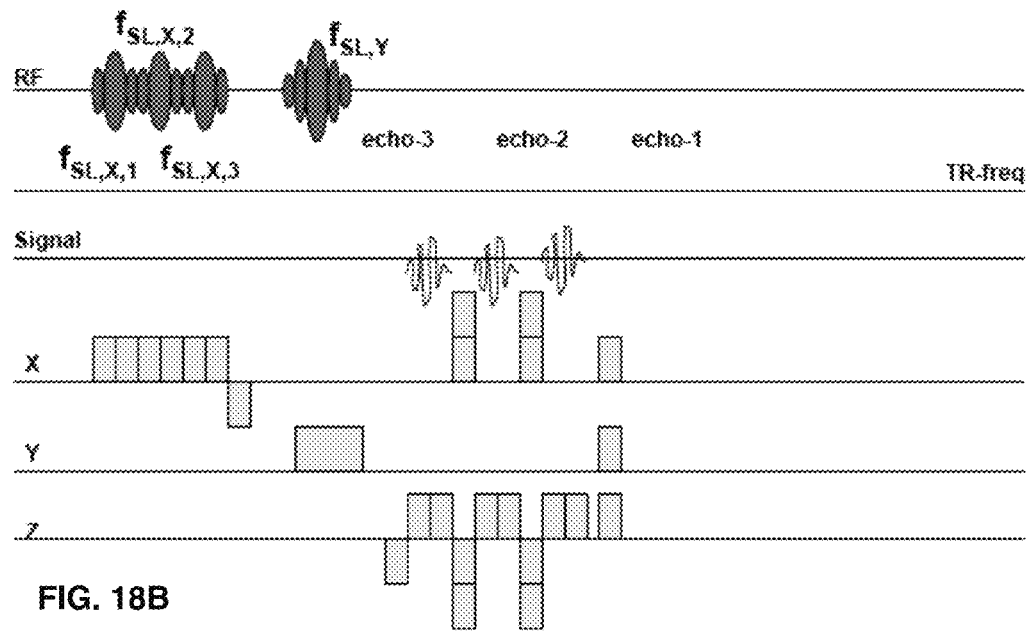
Figure 18C:
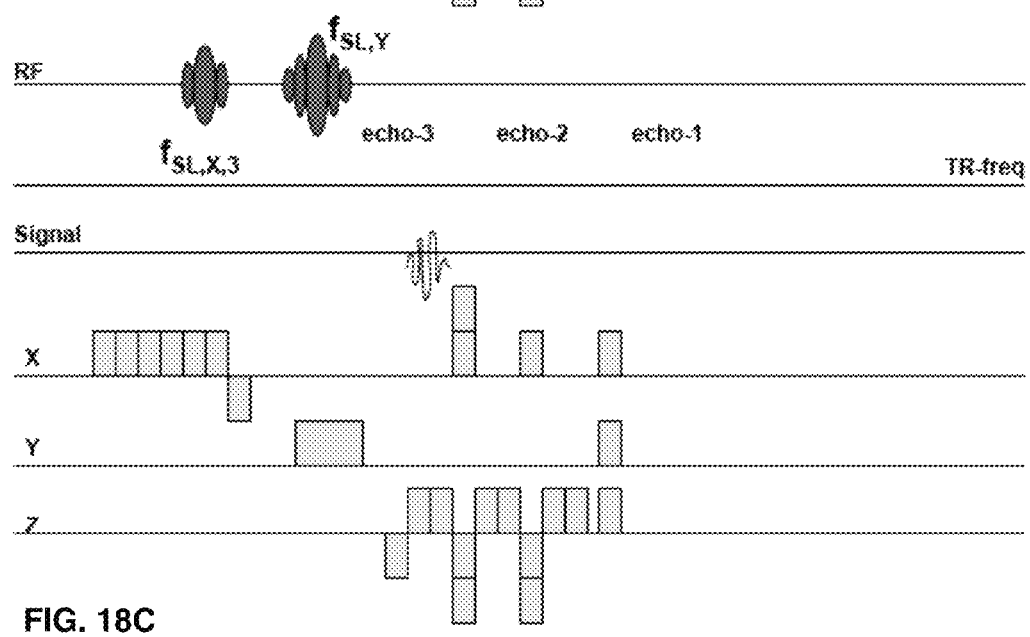
Figure 18D:
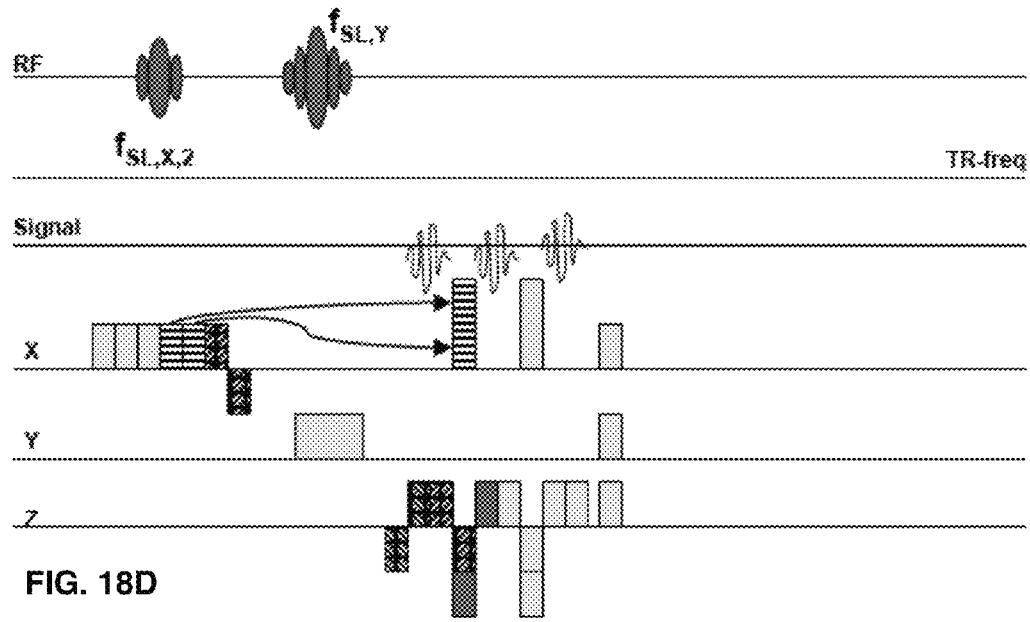
Figure 18E:
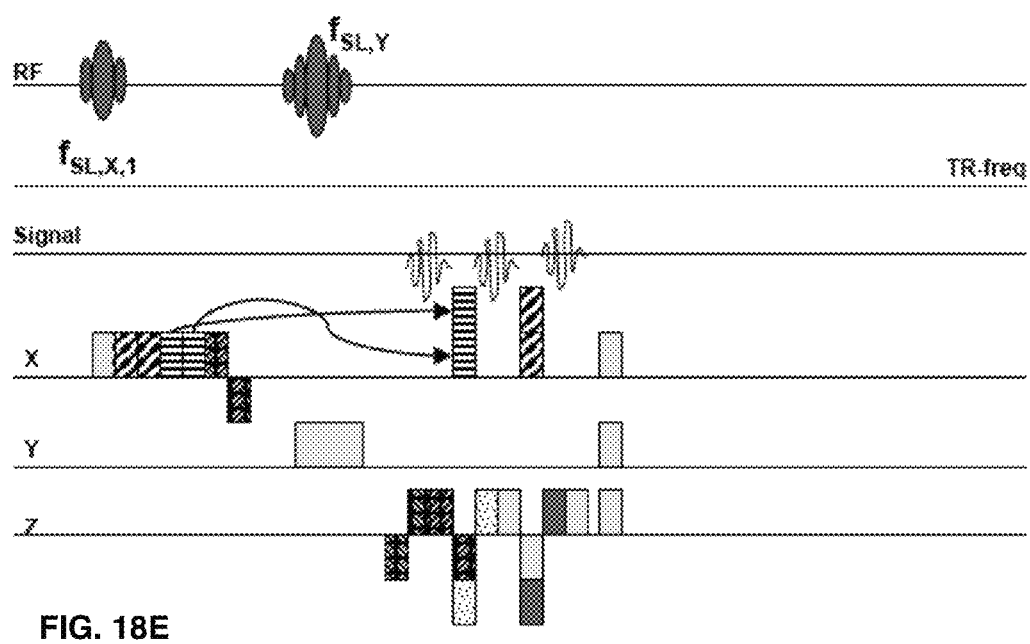

Also, FIGS. 18A to 18E illustrate multi-projection pulse sequences of type II and the gradient balancing thereof. As shown in FIG. 18A, type II pulse sequences differ from type I in that multi-slice selection is without slice refocusing on the X-axis. FIGS. 18B-18E illustrate balancing of the gradients for type II pulse sequences. Alternatively, FIG. 18F illustrates a multi-projection pulse sequence of type II which the first units differ from units 1 and 2 in FIG. 18A by utilizing: 1) single slice selection (X-axis) and 2) multi-slice selection with a train of inversion pulses (Y axis).

Figure 19:
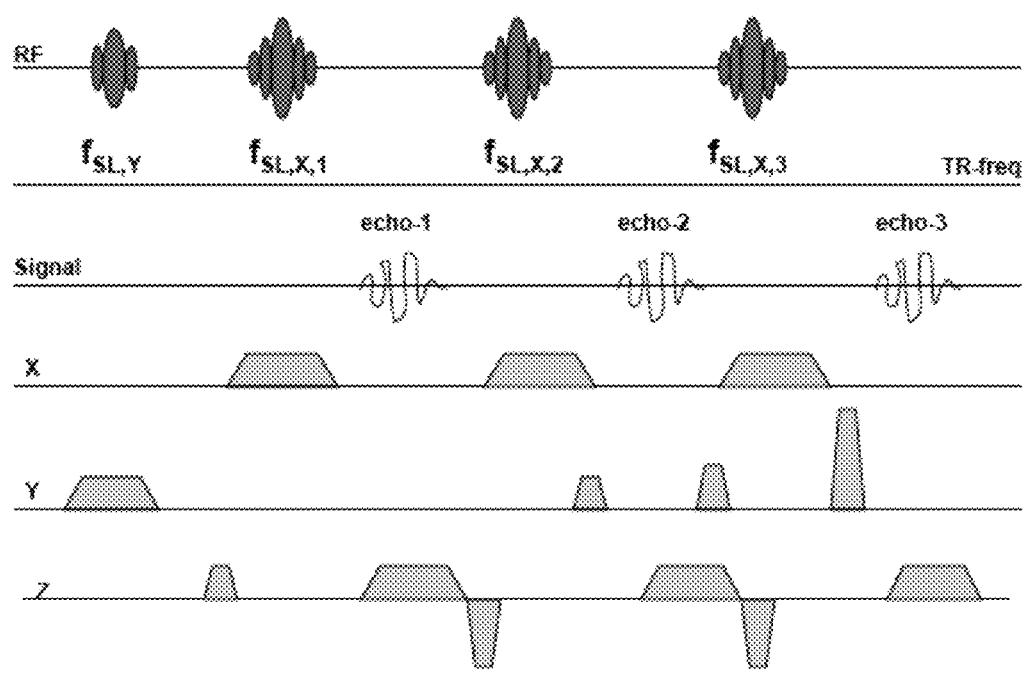
FIG. 19 depicts a type III multi-projection pulse sequence.

In addition, FIG. 19 illustrates multi-projection pulse sequences of type IIII. A pulse sequence is depicted for highly packed collection of projections (only 3 are shown). This sequence can be Turbo Spin Echo Like.

In yet another preferred embodiment there is provided fast dynamic 3D imaging with volume projections. For example, dual-projection MRI acquisition may be utilized. Generation of a 3D reconstruction entails two independent but interrelated processes. First, is the acquisition of the appropriate projections and the second is the reconstruction of the structure in a 3D volume. Originating from its inherent "true-3D" capabilities MRI provides certain benefits in collecting data and facilitating the 3D reconstruction of the imaged structure from its projections. First, the projections can be set to share a common axis which eliminates the need for transformation between the two projections. Moreover, the inherent co-registration of the spatial encoding on the two projections makes assignment of axes and matching straightforward. Second, the orientation of the imaged volume can be set to any arbitrary orientation relative to the structure which can be used to better resolve it, reducing the reconstruction algorithm workload. Third, the angle between the projection planes can be adjusted to any desired value and is not limited to orthogonal or otherwise preset values. Fourth, more than two planes can be used to resolve complex or highly tortuous structures.

Figure 20A:
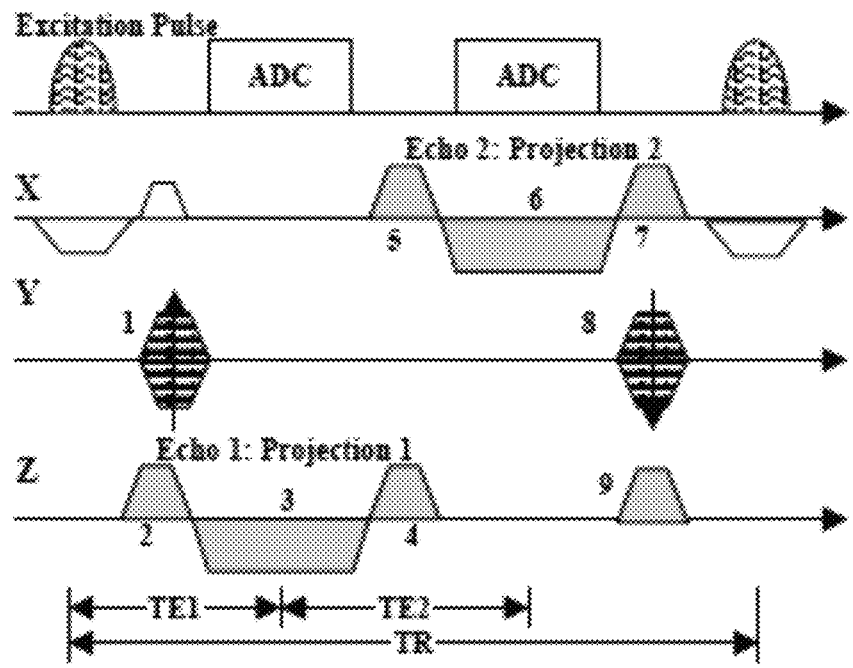
FIGS. 20A-20D depict type I pulse sequences for simultaneously collecting two or more projections after a single pulse (FIGS. 20A-20B) and for independently and simultaneously collecting two or more projections (FIGS. 20C-20D).
Figure 20B:
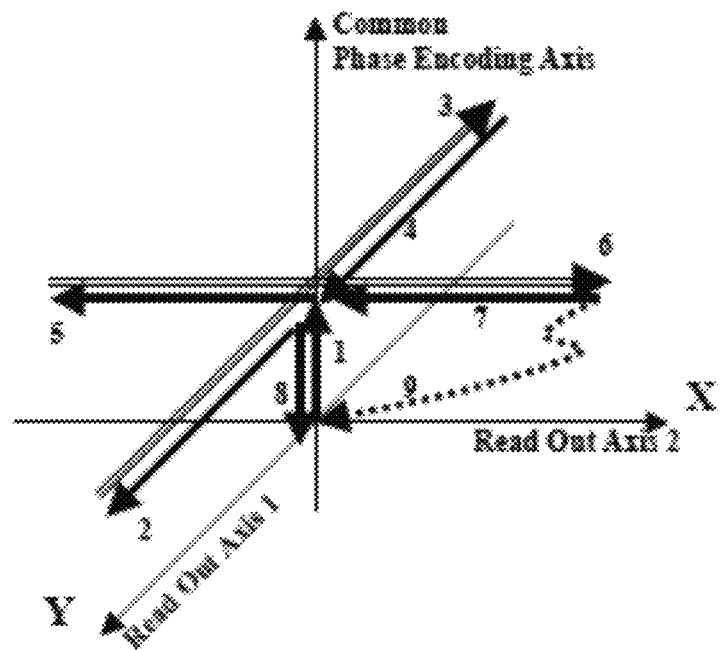
Figure 20C:
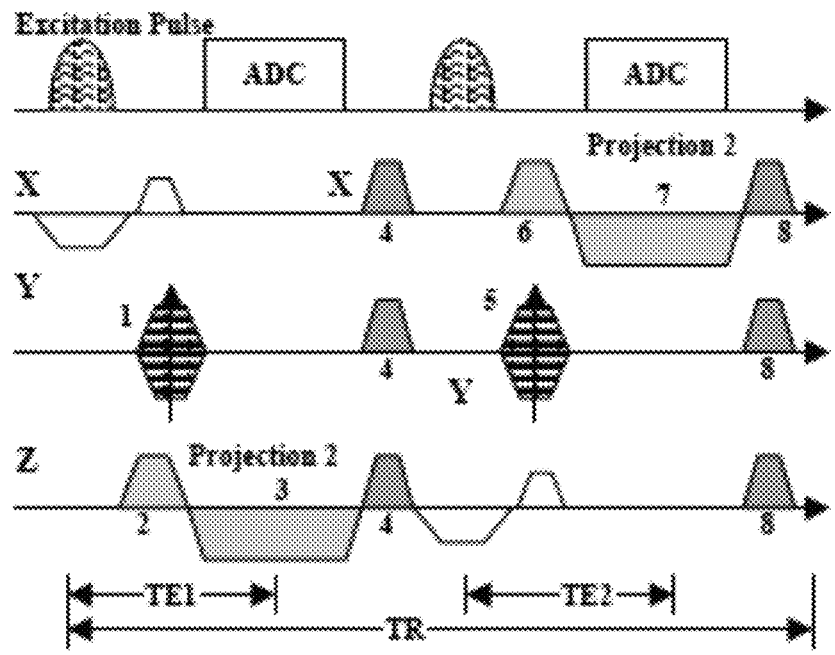
Figure 20D:
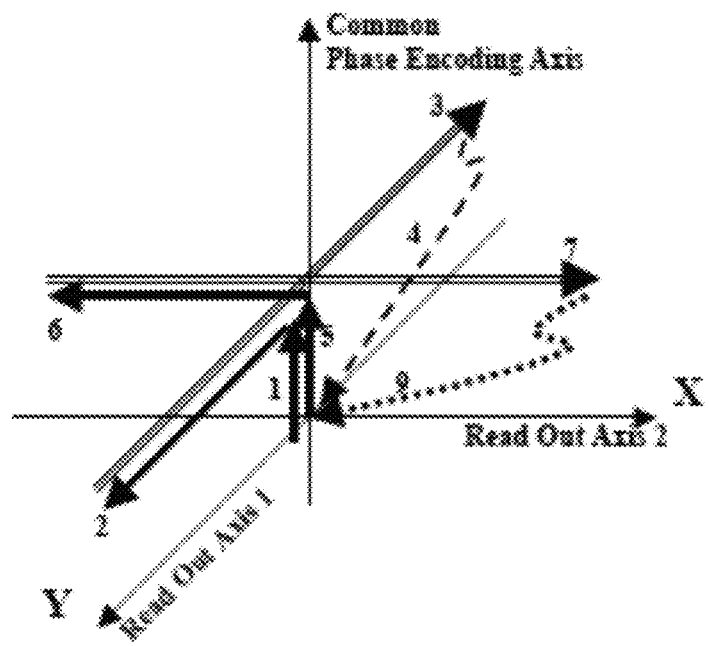

In a particular aspect an acquisition scheme based on two orthogonal projections may be utilized. For the dual-echo DPI Type I this is achieved with the two projections sharing the same phase encoding steps and axis, as shown in FIGS. 20A-20B. For each phase encoding step (axis Y), two echoes are collected, one for each projection, with the readout gradients applied along the conventional "slice selection" (axis X) and "frequency encoding" directions (axis Z). To ensure that the spins are at the origin of the k-space before the second echo, the read-out dephasing gradient is repeated along the read-out axis of the first echo. The single-echo DPI Type II, shown in FIGS. 20C-20D, independently simultaneously collecting two (or more) projections.

Three-dimensional reconstruction from two projections is a well studied problem used in the reconstruction of vessels from dual-plane fluoroscopy. In the general case, in fluoroscopic imaging the two projections are not orthogonal to each other and the centers of the corresponding FOV are not identical. In these cases, a series of transformations is applied to coregister the two projections to a common coordinate system of reference. Subsequently the structure is extracted and reconstructed using, for example, splines.

With MRI, the two projections are already inherently coregistered and, in particular, with the described pulse sequences and the center and size of the FOV are set identically. The inherent coregistration and coincidence of the FOV of the two projections results in a simple geometric problem. The first projection contains the spatial information of the imaged structure along the common phase axis (Y) and the first frequency encoding axis (Z). The second projection contains the spatial information of the imaged objects on the common phase encoding axis (Y) and the second frequency axis (X). Therefore, the two projections are matched along the common phase encoding direction. From this property, a reconstruction strategy can be devised. For each spatial position Y with SI greater than zero, identify the X and Y spatial positions that both have SI greater than zero. This will result to the original structure. The geometric equivalent of this process is to back-project the two projections in the 3D space and calculate their common space.

Although, using a dual projection to image and reconstruct a 3D structure is a rather simple and straightforward approach, it cannot resolve certain structural arrangements. Specifically, when the structure lies on a plane orthogonal to the common acquisition axis, i.e. the phase encoding axis, there is no unique solution using the two projections of the structure.

Figure 21:
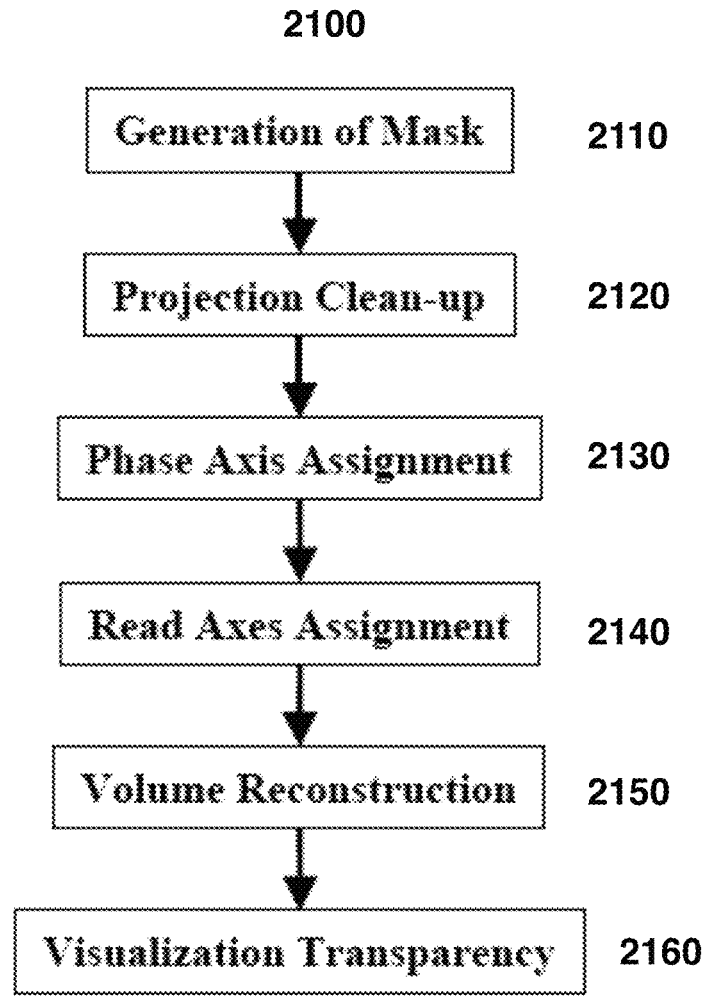
FIG. 21 is a flowchart for image reconstruction from dual projections.

A 3D reconstruction scheme was implemented, as shown in FIG. 21. Generally, the algorithmic steps 2100 entail generation of the mask 2110, projection clean-up 2120, phase axis assignment 2130, read axes assignment 2140, volume reconstruction 2150, and visualization transparency 2160. More particularly, this encompasses: 1) definition of the 3D volume which was acquired with the two projections, based on the center and size of the FOV and the size of the acquisition matrix; 2) segmentation of the contrast enhanced structure in both projections and generation of the corresponding spatial masks; 3) back-projection of the two masks into the 3D volume; and 4) calculation of the common space of the two back-projections defined with a logical AND logical operator. This algorithm is based on the assumption that the background signal is well saturated and, therefore, it is possible to segment out the imaged structure from the two 2D projection images.

The two projections were first segmented by thresholding based on the high structure-to-background contrast and then applying an edge detection. The result of the segmentation was two 2D masks. These masks were then extended orthogonally to their plane in the 3D volume. The common space between them was then defined with a logical AND operator to define the common space in the 3D volume.

In one example, the DPI sequences were evaluated on static and moving vessel-mimicking phantoms. Specifically, the reconstruction algorithm was first tested with a Gd-filled (3% Gd) tubing (i.d.=3.1 mm) mounted on a sphere filled with a saline solution or a partial saline solution and gadolinium. First, a multislice set was collected as a reference with a standard gradient recalled echo (GRE) sequence (TR/TE/a=5.47 ms/1.65 ms/50°; slice=2.5 mm FOV=250× 250 mm2; matrix=256×256). DPI imaging was then performed with a magnetization prepared dual-echo (TR/TE1/ TE2/50o=5.47 ms/1.65 ms/3.59 ms/50°; slice=250 mm FOV=250×250 $mm^2$; matrix=256×256) and single echo (TR/TE1/TE2/50°=5.47 ms/1.65 ms/3.59 ms/50°; slice=250 mm FOV=250×250 mm2; matrix=256×256) sequences.

Figure 22A:
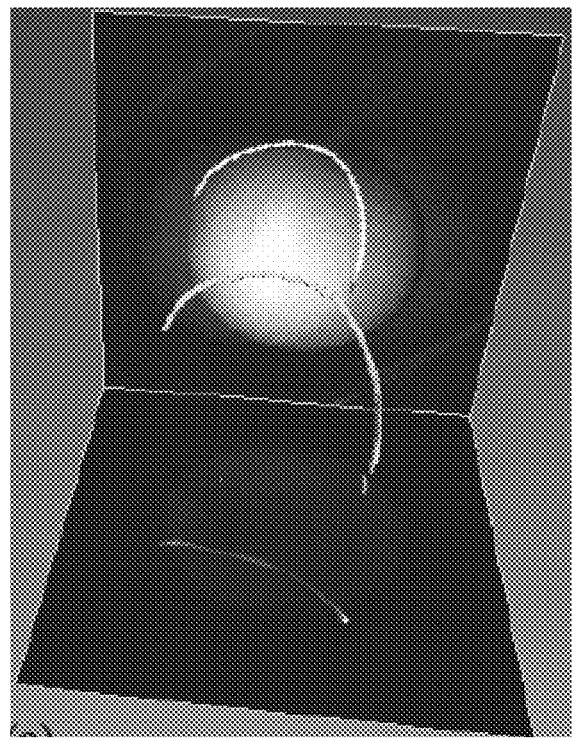
FIGS. 22A-22C illustrates the volume-projection method for 3D imaging of tubular structures reconstructed from a multi-slice set (FIG. 22A) and the imaging of a surgical robot via Dual Projection (FIG. 22B) and ultrafast 3D imaging (FIG. 22C).
Figure 22B:
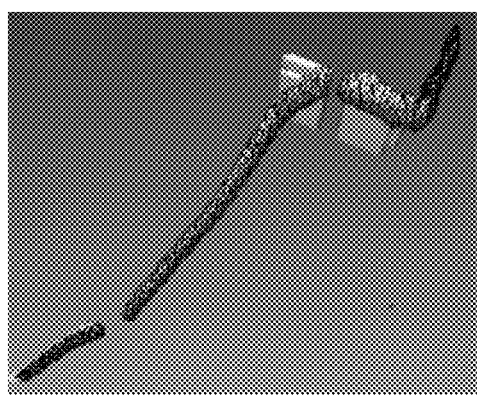
Figure 22C:
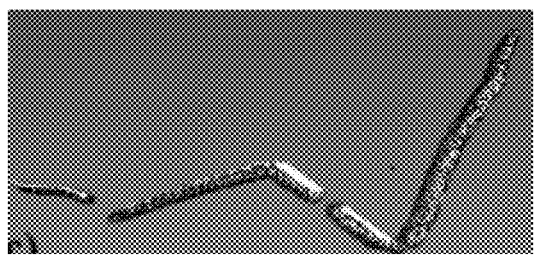

To eliminate the unwanted background signal, a magnetization preparation was performed with a Magnetization preparation consisted of a saturation pulse followed by two inversion pulses with interpulse delays of 16 ms, 101 ms and 67 ms, respectively, to suppress a wide range of species with long T1>250 ms. The sequences were also tested for imaging of moving vessel-mimicking tubing. Gd-filled tubes were attached on the end-effector of a seven degrees of freedom MR-compatible manipulator. 3D reconstruction was performed off-line with the algorithm described above using software developed in Matlab. Particularly, FIGS. 22A-22C show the structure reconstructed from a multi-slice set during an acquisition time of 1.2 minutes and images of the robot.

Figure 23:
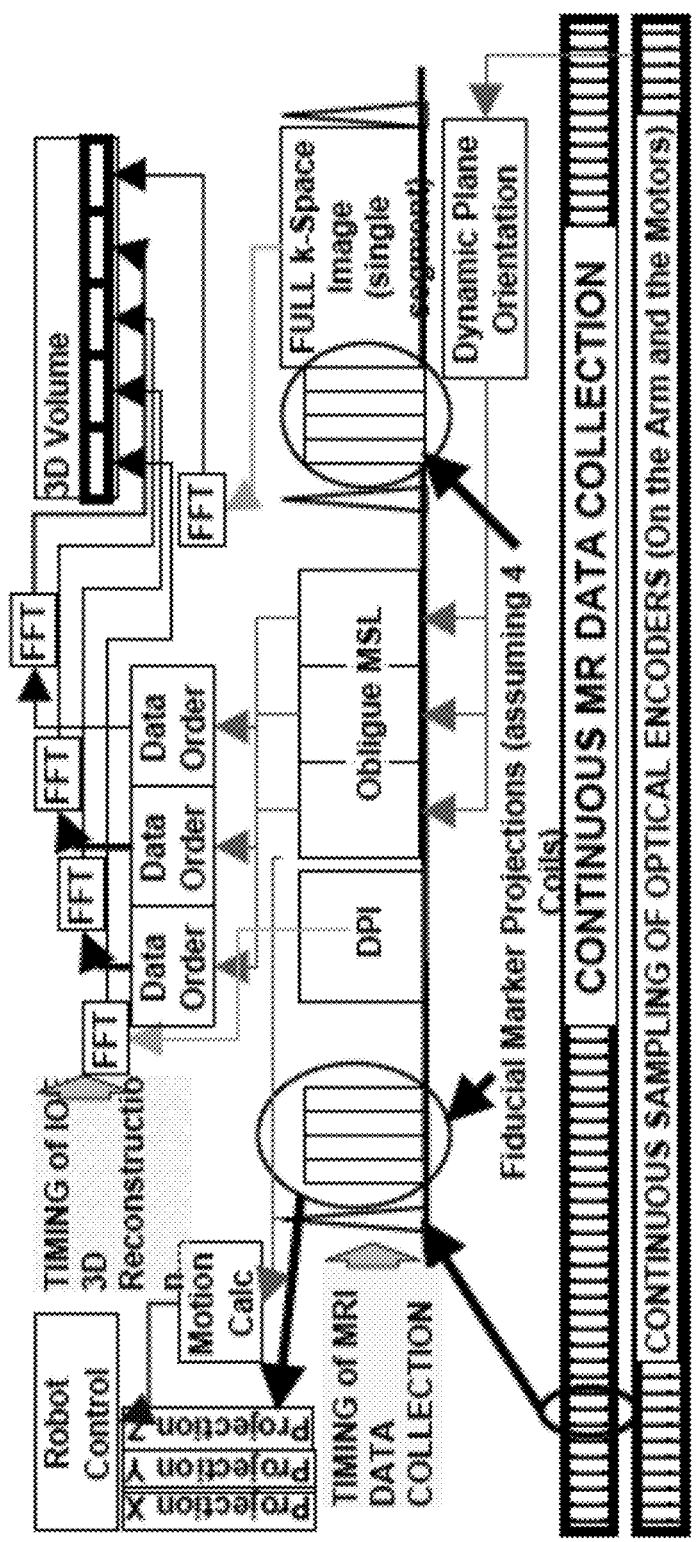
FIG. 23 is a timing diagram for a time-sharing MR protocol and a "First-Come-First-Served" reconstruction.

Also, in this preferred embodiment, the dual projection imaging can be incorporated into interleaved imaging protocols. For example, as shown in FIG. 23, a timing diagram is illustrated for time-sharing MR protocol and "First-Come-First-Served" reconstruction. Different blocks correspond to different pulse sequences, such as, collecting data which are FFT-ed directly (green arrows) or after ordering for segmented acquisition (red arrow) or used for data extraction (blue arrow) and then sent to refresh the IOE output in the GUI (black arrows), for real-time updating. The imaging planes are dynamically updated (pink line). Thus, importantly, the reconstruction and IOE update occurs in a "first-come-first-served" way.

Figure 24A:
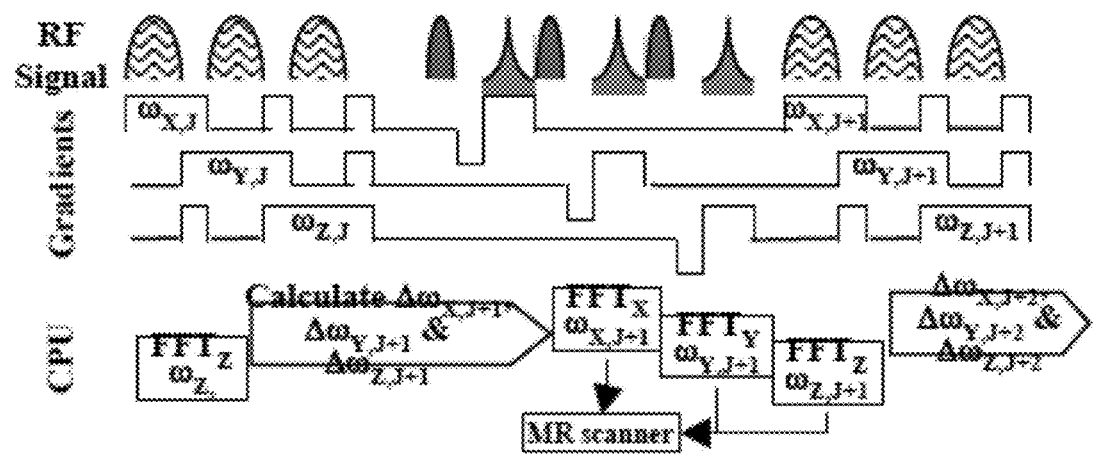
FIGS. 24A-24E depict a timing diagram (FIG. 24A) and the dependence of the tagging pulse angle versus the desired TI (FIG. 24B) and a timing imaging protocol utilizing multiple pulse sequences (FIGS. 24C-24E).
Figure 24B:
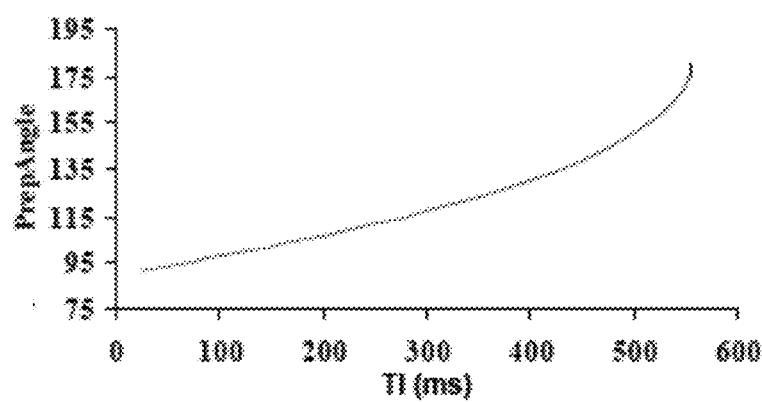
Figures 24C, 24D, 24E:
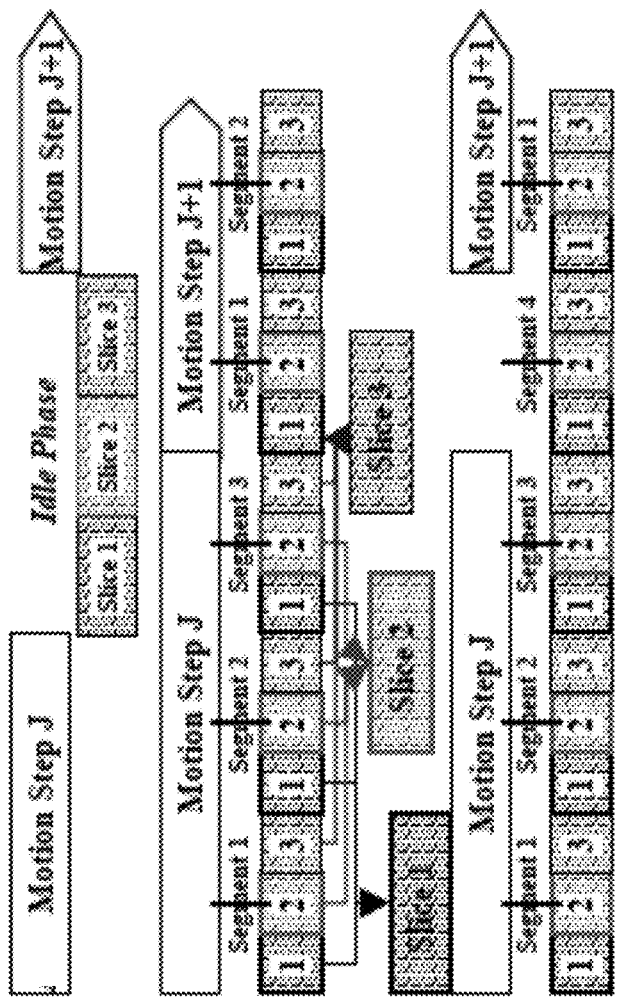

In addition, as shown in FIGS. 24A-24B, a timing diagram and the dependence of the tagging pulse angle versus the desired TI are depicted. The application of the tagging pulses can be set so that all three tags experience the same TI. The CPU timeline shows the elements of the processing which includes FFT of the projections, calculation of the tagging position and the J tagging pulse emission frequency (wX, J+1, wY, J+1 and wZ, J+1), download of emission frequencies to the scanner, and estimation of corrections for the next cycle J+2. A timing imaging protocol can combine multiple pulse sequences as illustrated in the imaging procedure shown in FIGS. 24C-24E.

Figure 25:
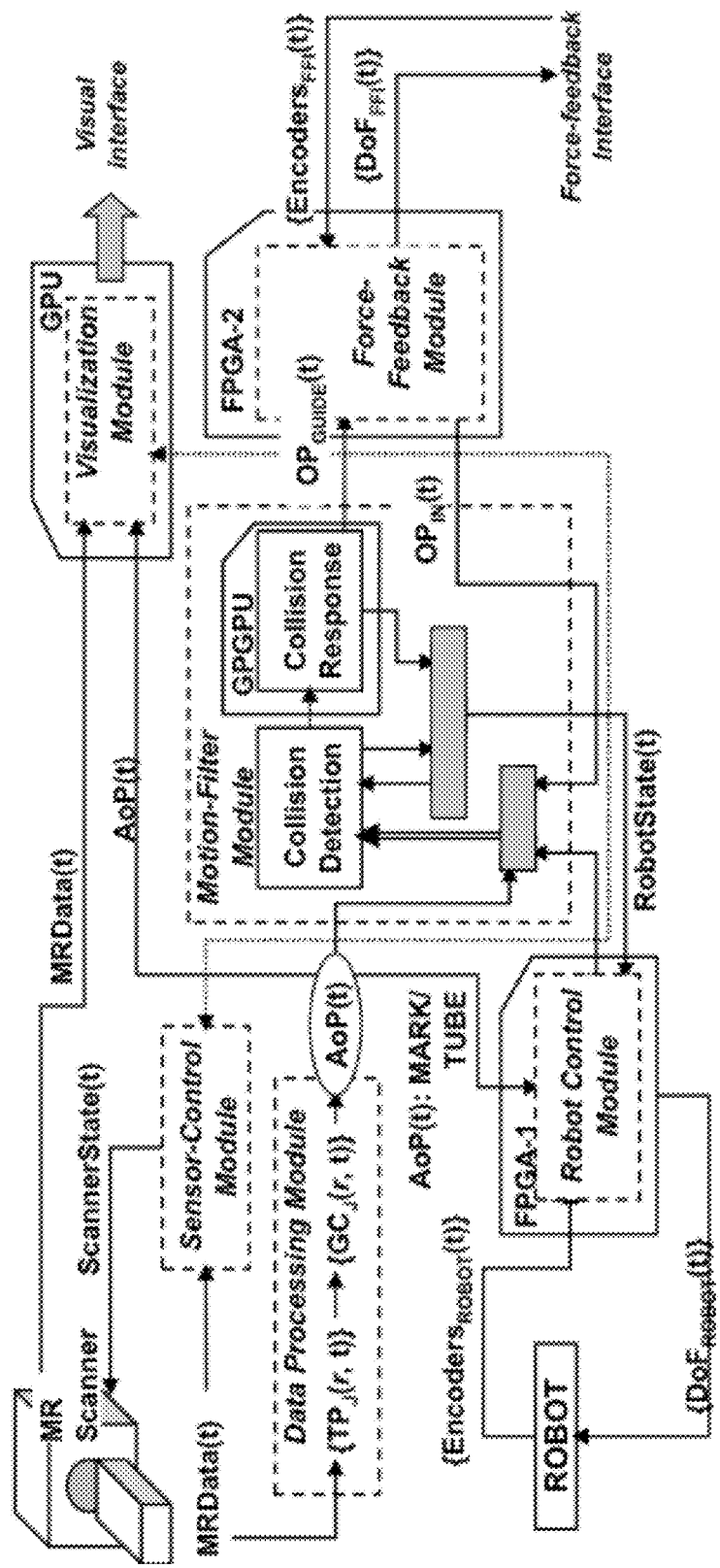
FIG. 25 depicts an Integrated Operation Environment (IOE) organization illustrating a computational framework for MR-guided and robot-assisted procedures.

Also in this preferred embodiment, the Integrated Operation Environment (IOE) organization is depicted in FIG. 25 that illustrates a computational framework for MR-guided and robot-assisted procedures that seamlessly link the sensor (MRI), the robot and the operator into a system. The IOE uses the stream of multimodal MR data, i.e. different information from the different MR pulse sequences described herein, that are refreshed with different rates. Its operation is a simple and computationally efficient approach, the "rolling window": as an MR dataset is collected, it substitutes the prior dataset of the same mode and is used with the rest of data to update the AoP scene. The IOE addresses in what form those multimodal data are represented for use in both robot control and augmenting human-interfacing. The IOE uses virtual constraints or fixtures, and extends this concept to incorporate the continuous feed of multimodal MR data to generate a dynamic model of the AoP (AoP(t)), in the form of the "access corridor". This is a 4D structure that extends from the site of entrance to the targeted anatomy. Within it, the robot can maneuver safely, i.e. without collision or harming vital structures or healthy tissue, and accurately reach the target or stay on-target for delivering an intervention. The information rendered on the access corridor will then be used for robot control and by the HIMI. The IOE further addresses of how to process multimodal MR data to generate access corridors from the plurality of the methods described herein: the RF coil markers (MARK) generate points, the projection columns (COLUMN) generate 1D projections and interleaved slices (INTERL) generate 2D images. The IOE generates tracker points, since it fits well with all methods and unifies algorithm implementation. Finally, the IOE uses the event-triggered response (in reference to the embodiment of FIG. 11) for updating the MR data acquisition strategy on-the-fly based on changes in the AoP. The above approaches are implemented in the form of software modules, running on dedicated threads, and interlink them in the framework, as shown in FIG. 25, and are configured to:

Process the real-time multimodal MR data feed MRData(t) and generate the 4D access corridors AoP(t), that implicitly describe all MR-generated information pertinent to tissue and robot.

Using the AoP(t), apply motion filtering (§5.3.3) to constrain the robot motion for safety and accuracy by (1) evaluating whether the operator commands $OP_{IN}(t)$ result to motion of the robot does not collide with the access corridor and is accurately approaching the target and (2) generating instructions for the robot RobotState(t) and for the force-feedback interface $OP_{GUIDE}(t)$.

Augment man-in-the-loop control by rendering the information generated to the operator, via force-feedback (FFI) and visual (VI) interfaces.

Identify changes in the tissue (MRData(t)) and robot (RobotState(t)) that require a new MR data acquisition strategy, select a new strategy (ScannerState(t)) and send it to the scanner.

Generate instructions for RobotState(t) for robot control.

The following references are cited herein.
1. Dumoulin et al. Magn Reson Med, 29:411-415 (1993).
2. Zhang et al. Magn Reson Med, 44:56-65 (2000).
3. Wong et al. J Magn Reson Imaging, 12:632-638 (2000).
4. Flask et al. J Magn Reson Imaging, 14:617-627 (2001).
5. A. E. Sonmez and N. V. Tsekos, An approach for Robot-Assisted Multimodal Biosensing and Imaging, in: Innovations in Cancer Prevention and Research Conference, Austin, Tex., 2011.
6. Sonmez et al. IEEE International Conference on Robotics and Automation, Shanghai, China, pp. 1133-1138 (2011).
7. Sonmez et al. International Society for Magnetic Resonance in Medicine (ISMRM) Joint Annual Meeting, pp. 3771 (2009).
8. Wacker et al. AJR Am J Roentgenol, 183:391-395 (2004).
9. Christoforou et al. Magn Reson Imaging, 25:69-77 (2007).

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A magnetic resonance image-guided and robot-assisted surgical system, comprising:
at least one computer processor;
at least one computer memory;
one or more robotic structures comprising a system registrable robot and/or an interventional tool;
a magnetic resonance scanner registered with the robot;
a plurality of modules configured for on-the-fly operation with the computer processor and memory that enable processor-executable instructions to:
collect and store MR-generated data about the robot and a tissue of interest in a patient;
establish a tissue boundary in an area of procedure;
dynamically monitor motion of the tissue boundary via the MR scanner disposed inside or outside a patient's body, using at least one signal intensity projection wherein the MR scanner tracks fiducial markers which are turned on, and wherein different fiducial markers are turned on and off dependent on the robot and/or tool position, and wherein the MR scanner monitors tissue-to-tissue or tissue-to-robot boundaries by:
exciting the tissue contained in at least a 3D column along a selected direction of the projection via radiofrequency pulsing, described, in an acquisition protocol, with the instance the pulse is applied, the type or shape of the pulse, the phase and the strength of the pulse; and
manipulating a magnetic field gradient, described with the spatial orientation of the gradient pulse, the instance it is applied, its shape, strength and duration of magnetic field gradient pulses;
acquiring raw data from the MR scanner; and
generating a 1D projection of the signal intensity from the raw data; and wherein the processor-executable instructions are further enabled to:
track a location of the robot or tool in reference to the area of procedure;
transmit the generated data to an operator of the system;
generate instructions for robot control and tracking from the generated data;
generate a view of the area of procedure and the robot during the surgical procedure for the operator; and wherein
the robot, the scanner, the modules and the operator communicate through a series of interfaces.

2. The system of claim 1, wherein the plurality of modules are further configured to enable processor-executable instructions to generate and visualize a 4D view of the area of the procedure from data acquired via the multi-modal sensors.

3. The system of claim 2, wherein the scanner is co-registered with a coordinate system.

4. The system of claim 1, wherein the steps of generating instructions for robot control and tracking and generating a view of the area of procedure and the robot during the surgical procedure further include the steps of:
process data about a status of the tissue and of the robot;
calculate changes thereto;
identify, algorithmically, events that trigger a change in data acquisition via instructions to compare the changes to a list of range-of-form values;
select a response to the event and devise an MR image acquisition strategy based thereon; and
transmit the MR image acquisition strategy to the MR scanner.

5. The system of claim 1, wherein the instructions to establish a tissue boundary operate to:
infuse, optionally, an exogenous contrast agent into the tissue;
select MR imaging sequences and set parameters to generate contrast differences within the tissue; and
generate the tissue boundary from one or more image projections obtained during magnetic resonance imaging.

6. The system of claim 1, wherein the on/off status of the markers are co-registered with a coordinate system of the MR scanner; and
motion filtering is applied to constrain robot motion.

7. The system of claim 6, wherein the coordinates of the markers relative to the coordinate system of the MR scanner are identified to detect locations thereof; wherein only a single marker location is detected for a localization step during robot tracking.

8. The system of claim 1, wherein manual control by the operator of the robot or the MR scanner is enabled.

9. The system of claim 1, wherein if more than one 3D column is included in a plane, the modules send a plurality of radiofrequency pulses and magnetic field gradient pulses so that the signal intensity profiles of all columns included in the plane are detected during the MR scanner data acquisition.

10. The system of claim 1, wherein the MR scanner can image natural tubular structures comprising the patient's body and artificial tubular structures.

11. The system of claim 10, wherein the instructions to image natural and/or artificial tubular structures with the MR scanner operate to:
generate contrast in the form of signal difference between the natural and/or artificial tubular structures and the background tissue or matrix, by performing the following steps:
infuse or load a contrast agent into the tubular structure or
modify the MR signal of the tubular structure, and eliminate or suppress the MR signal from background tissue or matrix;
acquire at least two 2D projections of the tubular structure containing 3D volumes that contain the structure with contrast agent; and
generate a 3D image from the 2D projections.

12. The system of claim 11, wherein when at least two 2D projections are acquired, and said projections are at any angle relative one to another.

13. The system of claim 11, wherein a selected sequence of radiofrequency pulses and magnetic field gradient pulses is used to acquire the 2D projection.

14. The system of claim 1, wherein the instructions for robot control operate to enable manual operator or automated control of the MR scanner for acquisition of the 2D projections under MR image-guidance.

15. A non-transitory computer-readable data storage medium storing computer executable instructions comprising the plurality of modules of claim 1.

16. A computer program product, tangibly embodied in the non-transitory computer readable medium of claim 15.

17. A magnetic resonance image-guided and robot-assisted surgical system, comprising:
at least one computer processor;
at least one computer memory;
one or more robotic structures comprising a system registrable robot and/or an interventional tool tools comprising the same;
a magnetic resonance scanner registered with the robot;
a plurality of modules configured for on-the-fly operation with the computer processor and memory that enable processor-executable instructions to:
collect and store MR-generated data about the robot and a tissue of interest in a patient;
establish a tissue boundary in an area of procedure;
dynamically monitor motion of the tissue boundary via the MR scanner disposed inside or outside a patient's body, and wherein the MR scanner tracks fiducial markers which are turned on, and wherein different fiducial markers are turned on and off dependent on the robot and/or tool position;
track a location of the robot or tool in reference to the area of procedure;
transmit the generated data to an operator of the system;
generate instructions for robot control and tracking from the generated data wherein the instructions for robot control operate, via manual operator control, to select at least one plane, at least one projection axis and at least one projection width; and, to select, concomitantly, 3D projection columns and group the same; and, wherein the instructions for robot control operate, via automatic control, to:
calculate magnetic resonance imaging acquisition parameters comprising pulse gradient timing, strength and duration of magnetic field gradient strength pulses; and, sequentially: update the acquisition parameters; acquire, dynamically, and analyze the projections; and generate a dynamic tissue model; and
calculate a dynamic corridor and trajectory by which to control the robot and/or guide the tool;
calculate a dynamic rendering of a haptic device;
produce an augmented reality of image guidance therefrom, and wherein the processor-executable instructions are further enabled to:
generate a view of the area of procedure and the robot during the surgical procedure for the operator; and
establish a plurality of interfaces among the robot, the scanner, the modules and the operator, which communicate through the interfaces.

18. A non-transitory computer-readable data storage medium storing computer executable instructions comprising the plurality of modules of claim 17.

19. A computer program product, tangibly embodied in the non-transitory computer readable medium of claim 18.

20. The system of claim 17, wherein the processor-executable instructions are enabled to generate and visualize a 4D view of the area of the procedure from data acquired via multi-modal sensors.

21. The system of claim 20, wherein the MR scanner is co-registered with a coordinate system.

22. The system of claim 17, wherein the steps of generating instructions for robot control and tracking and generating a view of the area of procedure and the robot during the surgical procedure further include the steps of:
process data about a status of the tissue and of the robot;
calculate changes thereto;
identify, algorithmically, events that trigger a change in data acquisition via instructions to compare the changes to a list of range-of-form values;
select a response to the event and devise an MR image acquisition strategy based thereon; and
transmit the MR image acquisition strategy to the MR scanner.

23. The system of claim 17, wherein the instructions to establish a tissue boundary operate to:
infuse, optionally, an exogenous contrast agent into the tissue;
select MR imaging sequences and set parameters to generate contrast differences within the tissue; and
generate the tissue boundary from one or more image projections obtained during magnetic resonance imaging.

24. The system of claim 17, wherein the on/off status of the markers are co-registered with a coordinate system of the MR scanner; and motion filtering is applied to constrain robot motion.

25. The system of claim 17, wherein the coordinates of the markers relative to the coordinate system of the MR scanner are identified to detect locations thereof; wherein only a single marker location is detected for a localization step during robot tracking.

26. The system of claim 17, wherein manual control by the operator of the robot or the MR scanner is enabled.

27. The system of claim 17 wherein if more than one 3D column is included in a plane, the modules send a plurality of radiofrequency pulses and magnetic field gradient pulses so that the signal intensity profiles of all columns included in the plane are detected during the MR scanner data acquisition.

28. The system of claim 17, wherein MR scanner can image natural tubular structures including the patient's body and artificial tubular structures.

29. The system of claim 28, wherein the instructions to image natural and/or artificial tubular structures with the MR scanner operate to:

generate contrast in the form of signal difference between the natural and/or artificial tubular structures and the background tissue or matrix, by performing the following steps:
infuse or load a contrast agent into the tubular structure, or
modify the MR signal of the tubular structure, and
eliminate or suppress the MR signal from background tissue or matrix;
acquire at least two 2D projections of the tubular structure containing 3D volumes that contains the structure with contrast agent; and
generate a 3D image from the 2D projections.

30. The system of claim 29, wherein when the two 2D projections are acquired, said projections are at an angle relative to one another.

31. The system of claim 29, wherein a selected sequence of radiofrequency pulses and magnetic field gradient pulses is used to acquire the 2D projection.

32. The system of claim 17, wherein the instructions for robot control operate to enable manual operator or automated control of the MR scanner for acquisition of the 2D projections under MR image-guidance.

* * * * *